(12) United States Patent
Rostami et al.

(10) Patent No.: US 7,255,887 B2
(45) Date of Patent: *Aug. 14, 2007

(54) USE OF BOWMAN BIRK INHIBITOR FOR THE TREATMENT OF MULTIPLE SCLEROSIS AND OTHER AUTOIMMUNE DISEASES

(75) Inventors: Abdolmohamad Rostami, Gladwyne, PA (US); Ann Kennedy, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 462 days.

This patent is subject to a terminal disclaimer.

(21) Appl. No.: 10/743,250

(22) Filed: Dec. 22, 2003

(65) Prior Publication Data

US 2004/0142050 A1  Jul. 22, 2004

(51) Int. Cl.
*A61K 35/78* (2006.01)
(52) U.S. Cl. .................................................... 424/757
(58) Field of Classification Search .................. None
See application file for complete search history.

(56) References Cited

U.S. PATENT DOCUMENTS

| | | | |
|---|---|---|---|
| 4,793,996 | A | 12/1988 | Kennedy et al. |
| 5,217,717 | A | 6/1993 | Kennedy et al. |
| 5,338,547 | A | 8/1994 | Kennedy et al. |
| 5,616,492 | A | 4/1997 | Kennedy et al. |
| 5,618,679 | A | 4/1997 | Kennedy et al. |
| 5,961,980 | A | 10/1999 | Kennedy et al. |
| 6,767,564 | B2 * | 7/2004 | Rostami et al. |

OTHER PUBLICATIONS

Atkinson, SJ, Ward, RV, Reynolds, JJ, "Cell-mediated degradation of type IV collagen and gelatin films is dependent on the activation of matrix metalloproteinases," *Biochem. J.* 288:605-611 (1992).
Bai, X.F., F.D. Shi, J. Zhu, B.G. Xiao, G. Hedlund, and H. Link, "Linomide-induced suppression of experimental autoimmune neuritis is associated with down-regulated macrophage functions," *J. Neuroimmunol.* 76:177 (1997).
Bar-Or A, Oliveira EM, Anderson DE, Hafler DA, "Molecular pathogenesis of multiple sclerosis," *J. Neuroimmunol.* 100:252-259 (1999).
Bever, CT Jr, Rosenberg, GA, "Matrix metalloproteinases; in multiple sclerosis: targets of therapy or markers of injury?" *Neurology* 53:1380-1381 (1999).
Billings PC, "Approaches to studying the target enzymes of anticarcinogenic protease inhibitors," In *Protease Inhibitors as Cancer Chemopreventive Agents*, Troll W, Kennedy AR (eds.), New York, Plenum Press, 1993, pp. 191-198.
Billings, PC, Brandon, DL, Habres, JM, "Internalization of the Bowman-Birk protease inhibitor by intestinal epithelial cells," *Eur. J. Canc.* 27:903-908 (1991B).
Billings, PC, Clair, WHS, Maki, PA, Kennedy, AR, "Distribution of the Bowman-Birk inhibitor in mice following oral administration," *Canc. Lett.* 62:191-197 (1992).
Billings, PC, Habres, JM, Liao, DC,. Tuttle, SW, "Human Fibroblasts Contain a Proteolytic Activity Which Is Inhibited by the Bowman-Birk Protease Inhibitor," *Cancer Res.* 50:5539-5543 (1991A).
Birk, Y, "Protease Inhibitors of Plant Origin and the Role of Protease Inhibitors in Human Nutrition," In *Protease Inhibitors as Cancer Chemopreventive Agents*. Troll W, Kennedy AR (eds). New York, Plenum Press, 1993, pp. 97-106.
Birk, Y, "Proteinase inhibitors from plant sources," *Meth. Enzymol.* 45:695-751 (1975).
Birk, Y, "The Bowman-Birk Inhibitor," *J. Peptide Protein Res.* 25:113-134 (1985).
Boccaccio, GL, Steinman, L, "Multiple sclerosis: from a myelin point of view," *J. Neurosci. Res.* [vol. 45]:647-654 (1996).
Bowman, DE, "Fractions derived from soybeans and Navy beans which retard tryptic digestion of casein," *Proc. Soc. Exp. Biol. Med.* 57:139-140 (1944).
Bowman, DE, "Further identification of bean trypsin inhibiting factors," *Arch. Biochem. Biophys.* 16:109-113 (1948).
Brosnan, CR, Caminer, W, Norton, WT, Bloom, BR, "Proteinase inhibitors suppress the development of experimental alleric encephalomyelitis," *Nature* 285:235-237 (1980).

(Continued)

*Primary Examiner*—Michele Flood
(74) *Attorney, Agent, or Firm*—Evelyn H. McConathy; Montgomery, McCracken, Walker & Rhoads, LLP

(57) ABSTRACT

Provided is a use for Bowman Birk Inhibitor (BBI), as administered in Bowman Birk Inhibitor Concentrate (BBIC), for the treatment of autoimmune diseases in a patient, wherein the disease is characterized by chronic inflammation, such as rheumatoid arthritis; and more particularly for the treatment of those diseases that are characterized by chronic neuroinflammation and/or demyelination, such as Multiple Sclerosis (MS) and Guillain Barre Syndrome (GBS). In addition, the present invention provides methods for using BBI/BBIC to reduce, inhibit, suppress or prevent the chronic inflammation in such patients; and more particularly, to reduce, inhibit, suppress or prevent the chronic neuroinflammation and demyelination that occurs when the patient's nerve tissues are affected by the disease.

6 Claims, 10 Drawing Sheets

OTHER PUBLICATIONS

Brostoff, SW, Burnett, P, Lampert, PW, Eylar, EH, "Isolation and characterization of a protein from sciatic nerve myelin responsible for experimental allergic neuritis," *Nat. New Biol.* 235:210-212 (1972).

Clements, JM, Cossins, JA, Wells, GM, Corkill, DJ, Helfrich, Y, Wood, LM, Pigott, R, Stabler, G, Ward, GA, Gearing, AJ, Miller, KM, "Matrix metalloproteinase expression during experimental autoimmune encephalomyelitis and effects of a combined matrix metalloproteinase and tumour necrosis factor-alpha inhibitor," *J. Neuroimmunol.* 74:85-94 (1997).

Constantinescu, C.S., Wysocka, M., Hilliard, B., Venyura, E.S., Lavi, E., Trinchieri, G. and Rostami, A., "Antibodies Against IL-12 Prevent Superantigen-Induced and Spontaneous Relapses of Experimental Autoimmune Encephalomyelitis," *J. Immunol.* 161:5097-5104 (1998).

Constantinescu, CS, Hilliard, B, Fujioka, T, Bhopale, MK, Calida, D, Rostami, AM, "Pathogenesis of Neuroimmunologic Diseases: Experimental Models," *Immunologic Res.* 17:217-227 (1998).

Cuzner ML, Opdenakker G, "Plasminogen activators and matrix metalloproteases, mediators of extracellular proteolysis in inflammatory demyelination of the central nervous systems," *J. Neuroimmunol.* 94:1-14 (1999).

Cuzner, MI, Norton, WT, "Biochemistry of demyelination," *Brain Pathol.* [vol. 6] 231-242 (1996A).

Dietsch, GN, Hinrichs, DJ, "Mast cell proteases liberate stable encephalitogenic fragments from intact myelin," *Cell. Immunol.* 135:541-548 (1991).

Evans et al., *Radiat. Res.* 132:259-262 (1992) "Protection against Metastasis of Radiation-Induced Thymic Lymphosarcoma and Weight Loss in C57Bl/6NCr1BR Mice by an Autoclave-Resistant Factor Present in Soybeans".

Frenkel, K, Chrazan, K, Ryan, CA, Wiesner, R, Troll, W, "Chymotrypsin-specific protease inhibitors decrease H202 formation by activated human polymorphonuclear leukocytes," *Carcinogenesis* 8:1207-1212 (1987).

Fujioka, T., E. Purev, and A. Rostami, "Chemokine mRNA expression in the cauda equina of Lewis rats with experimental allergic neuritis," *J. Neuroimmunol.* 97:51 (1999).

Fujioka, T., T. Jimi, B.A. Hilliard, E.S. Ventura, and A. Rostami, "The expression of cytokine mRNA in the cauda equina of Lewis rats with experimental allergic neuritis," *J. Neuroimmunol.* 84:223 (1998).

Gijbels, K, Galardy, RE, Steinman, L, "Reversal of experimental autoimmune encephalomyelitis with a hydroxamate inhibitor of matrix metalloproteases," *J. Clin. Invest.* 94:2177-2182 (1994).

Gladysheva, IP, Larionova, NI, Gladyshev, DP, Tikhonova, TV, Kazanskaia, NF, "The classical Bowman-Birk soy inhibitor is an effective inhibitor of human granulocyte alpha-chymotrypsin and cathepsin G," *Biochemistry* (Moscow) 59(4):513-518 (1994).

Gold, R., J.J. Archelos, and H.P. Hartung, "Mechanisms of immune regulation in the peripheral nervous system," *Brain Pathol.* 9: 343 (1999).

Halonen, T, Kilpelainen, H, Pitkanen, A, Riekkinen, PJ, "Lysosomal hudrolases in cerebrospinal fluid of multiple sclerosis patients," *J. Neurol. Sci.* 79:267-274 (1987).

Hartung, HP, Kieseier, BC, "The role of metalloproteinases in autoimmune damage to the central and peripheral nervous system," *J. Neuroimmunol.* 107:140-147 (2000).

Hauser, SL, Goodkin, DE, "Multiple Sclerosis and Other Demyelinating Diseases," In *Harrison's Principles of Internal Medicine*. Fauci et al. (eds). New York, McGraw-Hill, 1998, pp. 2409-2419.

Hawkins, JV, Emmel, EL, Feuer, A, Nedelman, MA, Harvey, CJ, Klein, HJ, Rozmiarek, J, Kennedy, AR, Lichtenstien, GR, Billings, PC, "Protease activity in a hapten-induced model of ulcerative colitis in rats," *Digestive Diseases and Sciences* 42:1969-1980 (1996).

Hewson, AY, Smith, T, Leonard, JP, Cuzner, ML, "Suppression of experimental allergic encephalomyelitis in the Lewis rat by the matrix metalloproteinase inhibitor Ro31-9790," *Inflamm. Res.* 44:345-349 (1995).

Ibrahim, MZM, Reder, AT, Lawand, R, Takash, W, Sallouh-Khatib, S, "The mast cells of the multiple sclerosis brain," *J. Neuroimmunol.* 70:131-138 (1996).

Kennedy, AR, "Anticarcinogenic activity of protease inhibitors: Overview," In *Protease-Inhibitors as Cancer Chemopreventive Agents*, Troll, W, Kennedy, AR (eds). New York, Plenum Press, 1993A, pp. 9-64.

Kennedy, AR, "Cancer prevention by protease inhibitors," *Preventive Med.* 22:796-811 (1993C).

Kennedy, AR, "Chemopreventive Agents: Protease Inhibitors," *Pharmacological Therapeutics* 78:167-209 (1998).

Kennedy, AR, "Mechanisms. of cancer prevention: Effects of protease inhibitors on protease and gene expression," In *Nutrients in Cancer Prevention and Treatment*, Prasad (ed) 1995B, pp. 71-82.

Kennedy, AR, "Prevention of carcinogenesis by protease inhibitors," *Cancer Res.* (suppl) 54:1999s-2005s (1994).

Kennedy, AR, "The evidence for soybean products as cancer preventive agents," *J. Nutr.* 125:733s-743s (1995C).

Kennedy, AR, Letter to the editor, *J. Nutr.* 126:584-585 (1996).

Kennedy, AR, Little, JB, "Protease, inhibitors suppress radiation induced malignant transformation in vitro," *Nature* 276:825-826 (1978).

Kennedy, AR, Manzone, H, "Effects of protease inhibitors on levels of proteolytic activity in normal and pre-malignant cells and tissues," *J. Cell. Biochem.* 22:188-194 (1995A).

Kennedy, AR, Szuhaj, BF, Newberne, PM, Billings, PC, "Preparation and production of a cancer chemopreventive agent, Bowman-Birk Inhibitor Concentrate," *Nutr. Cancer* 19:281-302 (1993B).

Kieseier, BC, Storch, MK, Archelos, JJ, Martino, G, Hartung, HP, "Effector pathways in immune mediated central nervous system demyelination," *Curr. Opin. Neurol.* 12:323-336 (1999).

Kremlev, S.G., A.I. Chapoval, and R. Evans, "Cytokine release by macrophages after interacting with CSF-1 and extracellular matrix proteins: characteristics of a mouse model of inflammatory responses in vitro," *Cell. Immunol.* 185:59 (1998).

Larionova, NI, Gladysheva, IP, Tikhonova, TV, Kazanskaia, NF, "Inhibition of cathepsin G and elastase from human granulocytes by multiple forms of the Bowman-Birk type of soy inhibitor," *Biochemistry* (Moscow) 58:1437-44 (1993).

Maeda, A, Sobel, RA, "Matrix metalloproteinases in the normal human central nervous system, microglial nodules, and multiple sclerosis lesions," *J. Neuropathol. Experimental Neurol.* 55:300-309 (1996).

Maki, et al., "Studies Related to the Potential Antigenicity of the Bowman-Birk Inihibitor, an Anticarcinogenic Protease Inihibitor Isolated From Soybeans", *Nutr. Cancer* 22:185-193 (1994).

Malkowicz, SB, McKenna, W.G., Vaughn, DJ, Wan, XS, Propert, KJ, Rockwell, K, Marks, SHF, Wein, AJ, Kennedy, AR, "Effects of Bowman-Birk Inhibitor Concentrate in patients with benign prostatic hyperplasia," *The Prostate* 48:16-28 (2001).

Meyskens, FL, Armstrong, WB, Wan, XS, Taylor, TH, Jenson, J, Thompson, W, Nguyen, QA, Kennedy, AR, "Bowman-Birk inhibitor concentrate (BBIC) affects oral leukoplakia lesion size, neu protein levels and proteolytic activity in buccal mucosal cells," *Proc. Amer. Assoc. Cancer Res.* 40:Abstract #2855 (1999).

Murphy, G, Atkinson, S, Ward, R, "The role of plasminogen activators in the regulation of connective tissue metalloproteinases," *Ann. N.Y. Acad. Sci.* 667:1-12 (1992).

Odani, S, Ikenaka, T, "Studies on soybean trypsin inhibitors VII. Disulfide bridges in soybean Bowman-Birk proteinase inhibitor," *J. Biochem.* 74:697-715 (1973).

Opdenakker, G, Van Damme, J. "Cytokine-regulated proteases in autoimmune diseases," *Immunol. Today* 15:103-107 (1994).

Owens, T., T. Renno, V. Taupin, and M. Krakowski, "Inflammatory cytokines in the brain: does the CNS shape immune responses?" *Immunol. Today.* 15:566 (1994).

Page, JG, Heath, JE, May, RD, and Martin, JF, "13-week toxicity study of Bowman Birk Inhibitor Concentrate (BBIC) in rats," SRI-CBE-94-060-7482, Southern Research Institute, Birmingham, AL (1994).

Page, JG, Rodman, LE, Giles, HD, Farnell, DR and Wood, RD, "13-week toxicity study of Bowman Birk Inhibitor Concentrate (BBIC) in dogs," SRI-CBE-94-135-7482, Southern Research Institute, Birmingham, AL (1994).

Raine CS, "The Dale E. McFarlin Memorial Lecture: the immunology of the multiple sclerosis lesion," *Ann. Neurol.* 36:S61-72 (1994).

Raine, CS, "Demyelinating Diseases," In *Textbook of Neuropathology*. Davis RL (ed) Baltimore, MD, Williams and Wilkins, 1990, pp. 356-358.

Rivers, TM, Sprunt, DH, Berry, GP, "Observations on attempts to produce acute disseminated encephalomyelitis in monkeys," J. Exp. Med. 58:39-53 (1933).

Romanic, AM, Madri, JA, "Extracellular matrix-degrading proteinases in the nervous system," *Brain Pathol.* 4:145-156 (1994).

Rosen, J.L., M. Brown, and A. Rostami, "Evolution of the cellular response in P2-induced experimental allergic neuritis," *Pathobiology* 60:108 (1992).

Rosen, JL, Brown, MJ, Hickey, WF, Rostami, AM, "Early myelin lesions in experimental allergic neuritis," *Muscle and Nerve* 13:629-636) (1990).

Rostami, AM, "Guillain-Barre syndrome: clinical and immunological aspects," *Springer Semin. Immunopathol.* 17:29-42 (1995).

Rostami, AM, Brown, MJ, Lisak, RP, Sumner, AJ, Zweiman, B, Pleasure, DE, "The role of Myelin P2 protein in the production of experimental allergic neuritis," *Ann. Neurol.* 16:680-685 (1984).

Rostami, AM, Gregorian, SK, Brown, MJ, Pleasure, DE, "Induction of severe experimental autoimmune neuritis with a synthetic peptide corresponding to the 53-78 amino acid sequence of the myelin P2 protein," *J. Neuroimmunol.* 30:145-151 (1990).

Serota, DG, One-year oral toxicity study of Bowman Birk Inhibitor Concentrate in Dogs., 560-058, MPI Researcch, Inc., Mattawan, MI (2000).

Serota, DG, "Six-month oral toxicity study of Bowman-Birk Inhibitor Concentrate in mice," 560-057, MPI Research, Inc., Mattawan, MI (2000).

Shang, X.Z., B.J. Lang, and A.C. Issekutz, "Adhesion molecule mechanisms mediating monocyte migration through synovial fibroblast and endothelium barriers: role for CD11/CD18, very late antigen-4 (CD49d/CD29), very late antigen-5 (CD49e/CD29), and vascular cell adhesion molecule-1 (CD106)," *J. Immunol.* 160:467 (1998).

St. Clair et al., "Suppression of Dimethylhydrazine-induced Carcinogenesis in Mice by Dietary Addition of the Bowman-Birk Protease Inhibitor", *Cancer Res.* 50:580-586 (1990).

Tikhonova, TV, Gladysheva, IEP, Kazanshaya, NF, Larionova NI, "Hydrolysis of elastin by human leukocyte elastase and cathepsin G: Inhibition by Bowman Birk type inhibitor," *Biochemistry* (Moscow) 59:1295-1299 (1994).

Vaday GG, Lider O, "Extracellular matrix moieties, cytokines, and enzymes: dynamic effects on immune cell behavior and inflammation," *J. Leukoc. Biol.* 67:149-159 (Feb. 2000).

Vaddi K- and R.C. Newton, "Regulation of monocyte integrin expression by Beta-family chemokines," *J. Immunol.* 153:4721 (1994).

van Hofe et al., "Inhibition of N-nitrosomethylbenzylamine-induced espohageal neoplasms by the Bowman-Birk protease inhibitor", *Carcinogenesis* 12:2147-2150 (1991).

Waksman, BH, Adams, RD, "Allergic neuritis? An experimental disease of rabbits induced by the injection of peripheral nervous tissue and adjuvants," *J. Exp. Med.* 102:213-236 (1955).

Wan et al., "Relationship between Protease Activity and *neu* Oncogene Expression in Patients with Oral Leukoplakia Treated with the Bowman Birk Inhibitor", Cancer Epidem. Biomarkers & Prevention 8:601-608 (1999).

Wan, XS, Koch, CJ, Lord, EM, Manzone, H, Billings, PC, Donahue, JJ, Odell, C, Miller, JH, Schmidt, NA, Kennedy, AR, "Monoclonal antibodies differentially reactive with native and reductively modified Bowman-Birk protease inhibitor," *J. Immunol. Meth.* 180:117-130 (1995).

Ware, JH, Wan, XS, Kennedy, AR, "The Bowman-Birk Inhibitor Suppresses Production of Superoxide Anion Radicals in Differentiated HL-60 Cells," *Cancer and Nutrition* 33:174-177 (1999).

Ware, JH, Wan, XS, Newberne, P, Kennedy, AR, "Bowman-Birk Inhibitor Concentrate reduces colon inflammation in mice with dextran sulfate sodium-induced ulcerative colitis," *Digestive Diseases and Sciences* 44:896-90 (1999).

Ware, JH, Wan, XS, Rubin, H, Schechter, NM, Kennedy, AR, "Soybean Bowman-Birk protease inhibitor is a highly effective inhibitor of human mast cell chymase," *Arch. Biochem. Biophys.* 344:133-138 (1997).

Weber, C., R. Alon, B. Moser, and T.A. Springer, "Sequential regulation of alpha 4 beta 1 and alpha 5 beta 1 integrin avidity by CC chemokines in monocytes: implications for transendothellal chemotaxis," *J Cell. Biol.* 134:1063 (1996).

Wucherpfennig KW, Catz I, Hausmann S, Strominger JL, Steinman L, Warren KG, "Recognition of the immunodominant myelin basic protein peptide by autoantibodies and HLA-DR2-restricted T cell clones from multiple sclerosis patients. Identity of key contact residues in the B-cell and T-cell epitopes," *J. Clin. Invest.* 100(5):1114-1122 (1997).

Yavelow, J, Collins, M, Birk, Y, Troll, W, Kennedy, AR, "Nanomolar concentrations of Bowman-Birk soybean protease inhibitors suppress X-ray induced transformation in vitro," *Proc. Nat'l. Acad. Sci. USA* 82:5395-5399 (1985).

Yavelow, J, Finlay, TH, Kennedy, AR, Troll, W, "Bowman-Birk soybean protease inhibitor as an anticarcinogen," *Cancer Res.* 43:2454-2459 (1983).

\* cited by examiner

USE OF BOWMAN BIRK INHIBITOR FOR THE TREATMENT OF MULTIPLE SCLEROSIS AND OTHER AUTOIMMUNE DISEASES

REFERENCE TO RELATED APPLICATION

This application claims priority to U.S. Provisional Application 60/230,568, filed Sep. 2, 2000.

FIELD OF THE INVENTION

This invention relates generally to novel use of the Bowman-Birk protease inhibitor for the treatment of neuroinflammatory autoimmune diseases, such as Multiple Sclerosis and Guillain Barre Syndrome, and other inflammatory autoimmune diseases, such as rheumatoid arthritis.

BACKGROUND OF THE INVENTION

The Bowman-Birk protease inhibitor (BBI) was first described decades ago (Bowman et al., Arch. Biochem. Biophys. 16:109-113 (1948); Bowman et al., Proc. Soc. Exp. Biol. Med. 57:139-140 (1944)). The BBI protein consists of 71 amino acid residues and 7 disulfide bonds, and it has a molecular weight of 7975 daltons (Odani et al., J. Biochem. 74:697-715 (1973)). BBI contains two functional protease inhibitor domains of different specificities. It inhibits both trypsin and chymotrypsin-like proteases (Birk et al., J. Peptide Protein Res. 25:113-134 (1985)), wherein one domain inhibits chymotrypsin-like proteases, and the other inhibits trypsin-like proteases. Chymase and tryptase are serine proteases, which are stored in the cytosol, from which they may be released upon stimulation by potentially proinflammatory cells, such as mast cells or macrophages.

The potent ability of certain serine protease inhibitors, such as BBI, to prevent the malignant transformation of cells was discovered in the laboratory of Dr. Ann Kennedy more than two decades ago (e.g., U.S. Pat. Nos. 5,217,717 and 5,338,547; Kennedy et al., Nature 26:825-826 (1978); Yavelow et al., Proc. Nat'l. Acad. Sci. USA 82:5395-5399 (1985); Kennedy, In Protease-Inhibitors as Cancer Chemopreventive Agents, Troll, W, Kennedy, A R (eds), New York, Plenum Press, 1993A, pp. 9-64; Kennedy, Pharmacological Therapeutics 78:167-209 (1998)).

Bowman Birk Inhibitor Concentrate (BBIC) is a soybean-derived extract enriched in the protease inhibitor, BBI, developed by Dr. Kennedy as a cancer chemopreventative agent (Kennedy et al., Nutr. Cancer 19:281-302 (1993B); U.S. Pat. Nos. 4,793,996; 5,217,717 and 5,338,547). The use of BBIC is preferred over crude soybean extract because: a) a very large amount of crude soybean extract would be required to contain amounts of BBI equivalent to the proposed dose of BBIC (approximately 2 quarts of soybean milk or the equivalent amount of tofu); b) crude soybean extract may also contain components which actually counter some of the anticipated beneficial effects of BBI.

Because the anti-carcinogenic activity of BBI is associated with the chymotrypsin-inhibitory domain of BBI (Yavelow et al., 1985), BBIC is quantitated in chymotrypsin inhibitor (CI) units (one CI unit is defined as the amount required to inhibit one mg of chymotrypsin (Kennedy et al., 1993B). In April 1992, BBIC was granted Investigational New Drug status (IND # 34671) from the Food and Drug Administration (FDA), and human trials to evaluate BBIC in several disease states are completed or in progress.

It is clear from animal studies that orally ingested BBI is absorbed and has systemic effects (reviewed in Kennedy, 1998). The structure of the BBI molecule is extremely stable (Birk, 1985; Birk, Meth. Enzymol. 45:695-751 (1975)), such that it survives the digestive process as an intact protease inhibitor capable of inhibiting proteolytic activities. This contrasts with a number of other protease inhibitors which do not survive the digestive process (Kennedy, unpublished). Approximately 50% of the ingested BBI is absorbed into the bloodstream.

BBIC is reportedly a better inhibitor of human chymases than any physiologic protease inhibitor described to date. In a recently finished Phase IIa oral cancer chemoprevention trial in patients with pre-malignant lesions known as oral leukoplakia, daily doses of BBIC led to a significant decrease in lesion size in a dose-dependent manner (Meyskens et al., Proc. Amer. Assoc. Cancer Res. 40:Abstract #2855 (1999).

Significantly, no toxicity has been observed due to BBIC in any human trial (see Table in Detailed Description). No antibodies against BBIC have been found in the sera of any patients receiving BBIC orally (Maki et al., Nutr. Cancer 22:185-193 (1994); Kennedy, personal communication; U.S. Pat. No. 5,961,980).

Absorbed BBI is measurable using antibodies to reduced BBI, produced by injection into experimental animals and utilized in immunoassays (Wan et al., 1995). BBI has been assessed in the blood, tissue and urine of rodents and dogs after the ingestion of BBIC permitting pharmacokinetic studies, although it has not yet been feasible to measure BBI levels in the blood of humans after oral BBIC dosing. However, it has been found in the urine, starting within several hours after a single oral dose (Wan et al., Cancer Epidem. Biomarkers & Prevention 8:601-608 (1999)). Of note, studies in orally-dosed animals have shown that some BBI can be subsequently found in the CNS even when the blood-brain barrier is intact (Kennedy, A R, personal communication).

BBIC has also proven in many instances to be an effective anti-inflammatory agent. BBIC has been demonstrated to have a suppressive effect on inflammation occurring in carcinogen-treated rodents rodents, as measured by the level of inflammatory infiltrates or lymphoid aggregates, in organs such as the colon and esophagus. For example, in the treatment of ulcerative colitis, an inflammatory bowel disease (Ware et al., Digestive Diseases and Sciences 44:896-90 (1999)), inflammation was significantly reduced following treatment with BBIC. Moreover, the chemical induction of ulcerative colitis in rats resulted in the induction of many proteolytic activities in the lesioned, inflamed tissues, on which BBI/BBIC reportedly showed a highly significant inhibitory effect on essentially all of the induced proteolytic activities (Hawkins et al., Digestive Diseases and Sciences 42:1969-1980 (1996)). In addition, BBI/BBIC treatment resulted in a suppression of cancer development and a reduction in the levels of inflammation, as measured by the level of inflammatory infiltrates or lymphoid aggregates in the colon (Kennedy et al., 1993A).

Several possible mechanisms by which BBIC may cause these effects have been proposed. First, it has been suggested that BBIC interferes with the inflammatory response by reducing the production of oxygen radicals in in polymorphonuclear leukocytes. Second, BBIC reportedly decreases interleukin-1 (IL-1) release, which is a well known, pro-inflammatory cytokine, participating in a wide variety of immune and inflammatory reactions. Third, BBIC has been shown to have the ability to inhibit the malignant transformation of cells; it has been hypothesized that BBI may inhibit cell transformation by affecting the function of certain oncogenes/proto-oncogenes (e.g., c-myc and c-fos). Nevertheless, little is known yet about either the cellular or molecular mechanisms by which BBIC can modulate or ameliorate autoimmune diseases.

BBI has been shown to efficiently inhibit several identified proteases released from human inflammation-mediating cells. These include human leukocyte elastase Tikhonova et al., *Biochemistry* (Moscow) 59:1295-1299 (1994); Larionova et al., *Biochemistry* (Moscow) 58:1437-44 (1993)) and human cathepsin G (Larionova et al., 1993; Gladysheva et al., *Biochemistry* (Moscow) 59(4):513-518 (1994)), which can efficiently destroy matrix molecules and severely damage tissues.

It is also known that BBI, as well as several other inhibitors of chymotrypsin proteolytic activity, have the ability to prevent the induction of superoxide anion radicals and hydrogen peroxide from stimulated human polymorphonuclear leukocytes and macrophage-like cells (Frenkel et al., *Carcinogenesis* 8:1207-1212 (1987); Ware et al., *Nutr. Canc.* 33:174-177 (1999)). Proteases and free radicals produced by macrophages are closely associated with the production of inflammation. For example, Multiple Sclerosis (MS) is characterized by inflammation and increased numbers of activated immunocytes of macrophage and T cell lineage (Hauser et al., In *Harrison's Principles of Internal Medicine*. Fauci et al. (eds). New York, McGraw-Hill, 1998, pp. 2409-2419).

Multiple Sclerosis (MS).

Multiple sclerosis (MS) is a neuroinflammatory disease of the central nervous system (CNS) characterized by chronic inflammation, demyelination and gliosis. Pathologically, MS is characterized by well-demarcated, macroscopic lesions, called plaques, in the brain white matter and, less frequently, gray matter. Acute lesions are characterized by perivenular cuffing and infiltration of T lymphocytes and macrophages, along with a few B cells and plasma cells. MS is reportedly an autoimmune disorder, likely triggered by environmental exposure in a genetically susceptible host. Complications from MS may affect multiple physiological systems and require profound changes in lifestyle for patients and their families. MS affects 350,000 Americans and is the second most frequent cause (after trauma) of neurologic disability in early to middle adulthood (Hauser et al., 1998).

MS is a complex disease, manifested in progressive or relapsing modalities, or combinations thereof. Proteolysis of myelin appears key to demyelination, which, in association with perivenular inflammation, is a major pathological feature in multiple sclerosis. Much of the investigative interest in MS has focused on the possible toxic effects on CNS myelin of locally accumulated lymphocytes and their components/products (Bar-Or et al., *J. Neuroimmunol.* 100:252-259 (1999); Wucherpfennig et al., *J. Clin. Invest.* 100(5): 1114-1122 (1997).

Proteases are associated with many facets of immune system function and immune system disorders (Cuzner et al., *J. Neuroimmunol.* 6:1-14 (1999); Vaday et al., *J. Leukoc. Biol.* 67:149-159 (2000)). A variety of proteases are increased in MS lesions, including lysosomal proteases and matrix metalloproteinases gelatinase A and B (MMP-2 and 9, respectively) (Cuzner et al., 1999; Halonen et al., *J. Neurol. Sci.* 79:267-274 (1987); Kieseier et al., *Curr. Opin. Neurol.* 12:323-336 (1999); Hartung et al., *J. Neuroimmunol.* 107:140-147 (2000); Bever et al., *Neurology* 53:1380-1381 (1999); Maeda et al., *J. Neuropathol. Experimental Neurol.* 55:300-309 (1996)).

Macrophages are also observed in association with chronic MS plaques (Hauser et al., 1998), even in early plaques, raising the possibility the macrophages may release myelinotoxic agents as well as serving a scavenger role (Cuzner et al., 1999; Raine, *Ann. Neurol.* 36:S61-72 (1994)). Macrophages are known to release MMPs, which are characteristically released from cells in the form of an inactive proenzyme, which must be activated by proteolytic removal of a propeptide (Atkinson et al., *Biochem. J.* 288:605-611 (1992); Cuzner et al., 1999; Hartung et al., 2000). This activation step can be carried out by other MMPs (Atkinson et al, 1992), or by serine proteases, such as plasmin, cathepsin G, chymase and trypsin (Cuzner et al., 1999; Hartung et al., 2000; Murphy et al., *Ann. N.Y. Acad. Sci.* 667:1-12 (1992); Brosnan et al., *Nature* 285:235-237 (1980)).

Mast cells also frequently accumulate in the cellular areas of MS plaques (Cuzner et al., 1999: Ibrahim et al., *J. Neuroimmunol.* 70:131-138 (1996)). Therefore, it is of interest that mast cells reportedly contain two serine proteases (cathepsin G [Ki=1.2 nM] and chymase [Ki=50 pM]), which are released with histamine upon degranulation. Active at neutral pH, the serine proteases may not only play an important initial role in the activation of MMPs in the pro-inflammatory enzymatic cascade, but they could account for the cleavage of the myelin components and release of the encephalitogenic fragments (Opdenakker et al., *Immunol. Today* 15:103-107 (1994)). Taken together, these observations indicate that mast cell proteases play a role in MS, and suggest that inhibition of serine protease activity is a potentially important therapeutic approach in MS, particularly if the production of naturally occurring anti-proteinases is impaired in MS lesional areas. Currently, BBI is the best known natural inhibitor of mast cell chymase (Ware et al., *Arch. Biochem. Biophys.* 344:133-138 (1997)).

Agents presently used prophylactically against MS relapses include interferon β1a, β1b, and copolymer-1. These agents are administered by subcutaneous or intramuscular injection on a daily or every other day basis. While generally well tolerated, the benefit of these therapies is limited to reducing the MS relapse rate by only about one third, when compared to placebo recipients. Moreover, neutralizing antibodies against interferon are produced within 12 months of initial treatment by significant numbers (20-40%) of those patients receiving current therapies, causing those patients to return to their pretreatment relapse rate. Acute relapses may be treated with a brief course of intravenous methylprednisolone, followed by oral prednisone. However, such short-term glucocorticoid therapy is associated with fluid retention, weight gain, gastric disturbances and emotional lability, which may require further treatment.

Chronically progressing MS is sometimes treated with immunosuppressants, such as methotrexate, azathioprine or cladribine. However, while these agents are of modest efficacy, regular monitoring of a patient's blood cell counts and liver functions during therapy is advised due to potential toxicities. Spasticity can be treated with agents, such as baclofen, diazapam, or clonazepam, but these are all of limited efficacy and can be counterproductive for patients who require a degree of rigidity for daily activities, such as walking.

Experimental Autoimmune Encephalomyelitis (EAE).

Experimental autoimmune encephalomyelitis (EAE) is a long-established disease model for MS. First described in monkeys (Rivers et al., *J. Exp. Med.* 58:39-53 (1933), this paradigm has been reproduced in several species, including mice and rats. EAE is induced by immunizing with myelin components, purified myelin proteins, or by peptide fragments resulting from the cleavage of stable encephalitogenic peptides from myelin, using a protease released from degranulated mast cells at neutral pH (Dietsch et al., *Cell. Immunol.* 135:541-548 (1991); Constantinescu et al., *Immunologic Res.* 17:217-227 (1998); Constantinescu et al., *J. Immunol.* 161:5097-5104 (1998)). EAE can also be induced 'passively' by adoptive transfer of antigen-reactive T helper cells from an immunized animal.

Histopathologically, EAE is characterized by CNS inflammation with macrophage and lymphocytic infiltrates and varying degrees of demyelination (Raine, In *Textbook of Neuropathology*, Davis R L (ed) Baltimore, Md., Williams and Wilkins, 1990, pp. 356-358). The disease manifests clinically with paralysis, beginning at the tail and spreading rostrally to the hindlimbs and forelimbs, and in advanced stages affects breathing and causes death.

Experimental Autoimmune Neuritis (EAN).

Oral BBIC administration has also demonstrated a profound inhibitory effect in rats with experimental autoimmune neuritis (EAN), an animal model of autoimmune peripheral nerve demyelinating disease having clinical, pathological and electrophysiological similarities to human Guillain-Barre Syndrome (GBS). GBS is an autoimmune, neuroinflammatory disorder related to MS, but affecting primarily the peripheral nervous system (PNS) (Shang et al., *J Immunol.* 160:467 (1998); Owens et al., *Immunol. Today* 15:566 (1994)).

EAN is a T cell mediated disease that can be transferred by CD4-positive antigen-specific $Th_1$ cells. Histopathologically, EAN is characterized by T cell and macrophage infiltration of the nerve roots (Weber et al., *J. Cell. Biol.* 134:1063 (1996)), demyelination and axonal injury (Waksman et al., *J. Exp. Med.* 102:213-236 (1955); Rosen et al., *Muscle and Nerve* 13:629-636 (1990); Vaddi et al., *J. Immunol.* 153:4721 (1994)). The infiltration of cells to the target tissue is accompanied with increased expression of adhesion molecules, pro-inflammatory cytokines and chemokines, both by the infiltrating cells and at the site of the immunological insult. Clinically, EAN manifests in rats first with tail paralysis, and progresses rostrally with paralysis of the hindlimbs, then the forelimbs. However, when model animals were treated with BBIC, a reduction was seen in both the extent of demyelination and the accumulation of inflammatory cells in the PNS tissue, comparable to the effect in EAE.

EAN is induced in rats by the injection of whole peripheral nerve tissues (Waksman et al., 1955; Rostami, *Springer Semin. Immunopathol.* 17:29-42 (1995)), a protein fraction (P0 or P2) isolated from peripheral nerve myelin (Brostoff et al., *Nat. New Biol.* 235:210-212 (1972); Rostami et al., *Ann. Neurol.* 16:680-685 (1984)), or by synthetic peptides corresponding to the myelin proteins (peptide SP26 corresponds to the 53-78 amino-acid sequence of the myelin P2 protein) (Rostami et al., *J. Neuroimmunol.* 30:145-151 (1990).

Inflammatory autoimmune diseases, such as rheumatoid arthritis, and neuro-inflammatory autoimmune diseases, such as Multiple Sclerosis (MS) and Guillain Barre Syndrome, exert a major impact on the health of the American population. MS is particularly devastating because of the extensive morbidity and premature fatalities in relatively young, productive individuals afflicted with the disease. Current therapeutic approaches to MS, such as treatment with glatiramer or beta-interferon (INF-β) have resulted in only relatively modest benefits. However, the disease is not well controlled. The use of other therapeutic agents, such as corticosteroids and immunosuppressive agents, in recent years has also been limited by inconsistent benefits and/or cumulative toxic effects. Therefore, from both a social and a medical standpoint, there is a major need for a reliable and effective non-toxic method for treating the chronic inflammatory effects that play pathogenic roles in MS, GBS, and other autoimmune diseases.

SUMMARY OF THE INVENTION

The present invention provides a non-toxic therapy and a novel use for Bowman Birk Inhibitor (BBI), as administered in Bowman Birk Inhibitor Concentrate (BBIC), for the treatment of autoimmune diseases characterized by chronic inflammation in a patient, such as rheumatoid arthritis, and more particularly for the treatment of those diseases that are characterized by chronic neuroinflammation and/or demyelination, such as Multiple Sclerosis (MS) and Guillain Barre Syndrome (GBS). In addition, the present invention provides methods for using BBI/BBIC to reduce, inhibit, suppress or prevent the chronic inflammation in such patients; and more particularly, to reduce, inhibit, suppress or prevent the chronic inflammation and demyelination that occurs when the patient's nerve tissue is affected by the disease. Such neuroinflammation may affect the central nervous system or peripheral nervous system of the patient.

The method is, therefore, provided for the treatment of chronic autoimmune diseases in the patient characterized by inflammation, such as rheumatoid arthritis, and more particularly for the treatment those diseases that are characterized by neuroinflammation and/or demyelination, such as Multiple Sclerosis (MS) and Guillain Barre Syndrome (GBS).

In a preferred embodiment of the invention, the method of using BBI/BBIC to treat a disease is applied to a human patient, although other animals, particularly mammals may also be treated.

In another preferred embodiment of the invention, the method is provided in which the Bowman Birk Inhibitor is administered orally. In certain preferred embodiments, BBI/BBIC is administered to the patient with a carrier, or it is administered with another therapeutic agent, drug, medicament or treatment In yet another preferred embodiment of the invention the method is provided in which the Bowman Birk Inhibitor (BBI) is administered as Bowman Birk Inhibitor Concentrate (BBIC). The BBI is provided as an enriched concentrate extracted from a legume, preferably as an enriched concentrate extracted from soybeans (BBIC).

Also provided in the present invention is a method for treating inflammation in an animal model of an induced inflammatory disease comprising administering to the animal an amount of Bowman Birk Inhibitor effective to reduce, inhibit, suppress or prevent the chronic inflammation. As above, the method is preferably applied when the chronic inflammation is inflammation of neural tissue, as part of either the central nervous system or the peripheral nervous system of the patient. The present method is particularly useful when used to reduce, inhibit, suppress or prevent demyelination of the nerve tissue of the patient. In a preferred embodiment of the present method, the induced disease is Experimental Autoimmune Encephalomyelitis (EAE) or Experimental Autoimmune Neuritis (EAN).

Not only does the use of BBIC, alone or in concert with other agents or treatments, provide a major step forward in the treatment of MS and other chronic inflammatory autoimmune diseases, including neuroinflammatory diseases, its use will permit further studies into the nature of the inflammatory reactions involved in such diseases. Thus, the invention further provides for the use of BBI/BBIC in vitro with cells from patients or animal subjects affected by or subject to induced inflammatory responses, such as EAE or EAN, as well as chronic inflammatory autoimmune diseases, such as rheumatoid arthritis, or chronic neuroinflammatory autoimmune diseases, such as MS and GBS.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s) which are presently preferred. It should be understood, however, that the invention is not limited to the precise arrangements and instrumentalities shown.

FIGS. 4A, 4E, and 4I, side light scatter (SSC) plots and gates, depict isotype controls. EAN splenocytes were stained and analyzed by FACS for the expression of CD3 (FIGS. 4B-4D), CD4 (FIGS. 4F-4H), and CD8 (FIGS. 4J-4L). The numbers refer to the mean fluorescence intensity (MFI) and average number of positive cells from eight (8) different experiments.

FIGS. 5A and 5E, side light scatter (SSC) plots and gates, depict isotype controls. EAN splenocytes were stained and analyzed by FACS for the expression of CD11b (FIGS. 5B-5D) and ED1-like antigen (FIGS. 5F-5H). The numbers refer to the MFI and average number of positive cells from eight (8) different experiments. As shown, BBIC up-regulated expression of ED1-like antigen (FIG. 5H) relative to the expression by either untreated cells (FIG. 5F) or after 72 h incubation with SP26 (FIG. 5G), but BBIC had no effect on CD11b expression (FIG. 5D) compared either with SP26-untreated (FIG. 5C) or -treated cells (FIG. 5B).

In FIGS. 8B-8E, R1 cells are shown; in FIGS. 8F-8I, R2 cells are shown. After 72 hours in culture, cells were examined for apoptotic response without any treatment (FIGS. 8B and 8F), treatment with SP26 (FIGS. 8C and 8G), or BBIC (FIGS. 8D and 8H) alone, and in the presence of a combination of SP26 and BBIC (FIGS. 8E and 8I). The percentage of apoptotic cells is shown, calculated as differences between apoptosis in stained cell populations and negative controls developed for each particular group. The representative experiment of three (3) is shown.

DESCRIPTION OF PREFERRED EMBODIMENTS OF THE INVENTION

Figure 1:
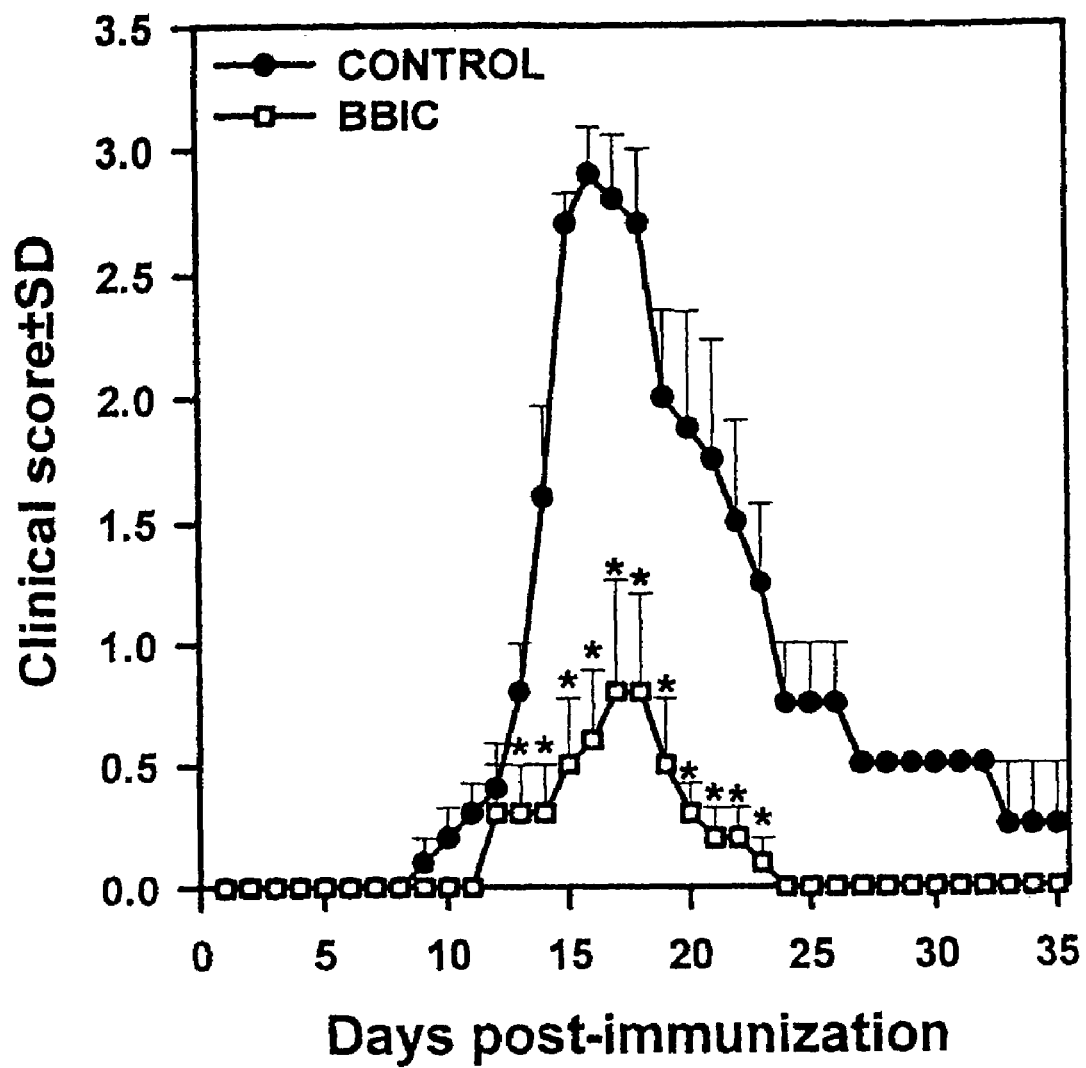
FIG. 1 graphically depicts the effect of treatment of active EAN with BBIC. The clinical score is shown. The data are shown as mean clinical score at any particular time point (n=6 for each group at each time point; * p<0.05; compared to untreated animals).

The invention provides a novel method for the use of BBI/BBIC to treat patients with chronic inflammatory autoimmune disease, such as, but limited to, rheumatoid arthritis; and particularly to treat patients with diseases characterized by neuroinflammation and/or demyelination, such as, but not limited to Multiple Sclerosis (MS) and Guillain Barre Syndrome. The method of using BBI/BBIC effectively reduces, inhibits, suppresses or prevents inflammation in such a patient, and when the disease is characterized by neuroinflammation, the method of using BBI/BBIC effectively reduces, inhibits, suppresses or prevents neuroinflammation and/or demyelination of the nerve tissue of the patient.

In a preferred embodiment of the invention, the method is provided in which BBI/BBIC is used to treat an animal subject in which an inflammatory disease is induced, such as Experimental Autoimmune Encephalomyelitis (EAE) or Experimental Autoimmune Neuritis (EAN). The application of the present method of treating inflammation and neuroinflammation in such an animal subject, as displayed by the alleviation or elimination of paralysis, is also an accepted animal model for the responses found in human patients with MS, GBS, or other chronic inflammatory autoimmune diseases.

The use of BBIC for the treatment of MS according to a preferred embodiment of the present invention was selected for a combination of reasons including, but not necessarily limited to, the following. First, there exists a substantial body of evidence that demonstrates increased local protease deposition in the MS lesions, including the presence of macrophages in the cellular zone of early plaque lesions. This protease activity includes neutral serine proteases, such as plasmin, chymase and cathepsin G. Such serine proteases both have a directly damaging effect on myelin, (Romanic et al., Brain Pathol. 4:145-156 (1994)), and they convert metalloproteinase (MMP) pro-enzymes into functionally active enzymes, with potentially toxic effects.

Second, it is not yet known exactly how much BBI enters the human CNS after oral BBIC dosing. However, it is anticipated that BBI entry is increased in the CNS of patients affected by MS because of localized decreases in the blood-CNS barrier in such areas. Also, based on the background evidence reviewed above, one would also expect BBI to inhibit entry of immune/inflammatory cells into the CNS, with potential for reduction of the pathogenic effects of such cells.

Third, in preliminary studies, BBIC has been shown to be a potent inhibitor of several serine proteases. Because neutral serine proteases appear to play an important initial role in the activation of MMPs in the pro-inflammatory enzymatic cascade described above, inhibition of such serine protease activity is potentially important to the therapeutic approach in MS. As reviewed (Cuzner et al., 1999; Hartung et al., 2000), this is significant because extracellular proteolysis has been associated with several effects of importance in inflammatory demyelination, which although not intended to be limiting, include:

(1) proteolysis of myelin components, such as myelin basic protein (MBP);
(2) generation of encephalitogenic peptides which could induce autoimmune reactions;
(3) proteolysis of basement membranes, leading to increased extravasation of humoral factors and cells (decreased blood-brain barrier), implying an important role for MMP's in the process of T-cell migration into the CNS;
(4) proteolysis of the extracellular matrix-leading to enhanced inflammatory cell migration after entry into the CNS; and
(5) proteolysis of cell surface molecules on resident cells leading to cytolysis; and
proteolytic activation of other zymogens.

Moreover, the therapeutic modulation of serine protease activity may be particularly important in MS because the inhibition of serine proteases by naturally occurring anti-proteinases may be impaired in MS lesional areas.

These observations are consistent with the notion that mast cell proteases also play a role in MS. If so, BBI, which is a highly effective inhibitor of cathepsin G and chymase, two of the major mast cell proteases, provides an excellent agent of intervention at this point.

BBIC administration has demonstrably inhibited both the clinical and pathologic expression of EAE and EAN, which are the recognized animal models for autoimmune disorders characterized by neuroinflammation and demyelination—MS and Gullain Barre Syndrome. Inhibition of plasmin formation and synthetic inhibitors of MMP activity have both been shown to reduce severity of clinical EAE (Cuzner et al., 1999; Gijbels et al., J. Clin. Invest. 94:2177-2182 (1994); Clements et al., J. Neuroimmunol. 74:85-94 (1997); Hewson et al., Inflamm. Res. 44:345-349 (1995)). MMP inhibitors, including naturally occurring agents such as TIMP, may be expected to work at two levels: 1) by blocking extravasations of inflammatory cells into the CNS, and 2) by inhibiting effector properties of lymphocytes and macrophages in the initial stage of inflammation in the MS lesion, without an apparent inhibitory effect on the sensitization of T cells to myelin components (Cuzner et al., 1999).

Since reactive oxygen species (ROS) can damage both oligodendroglia and myelin in CNS inflammatory reactions, inhibition of ROS formation by BBI offers another ameliorative effect in MS.

Fourth, in human trials involving patients with oral leukoplakia, benign prostatic hyperplasia, and ulcerative colitis since 1992, BBIC has not caused, or been associated, with any toxic effects or induced immune response when used at doses approximately comparable to those employed in the present invention.

Fifth, BBIC is a reasonably well-defined patented product, classified by the FDA as an Investigational New Drug for use in humans. An adequate supply of BBIC is available for studies of sufficient length to determine: a) the safety of BBIC in MS patients, and b) acquire data relating to therapeutic efficacy.

Consequently BBI/BBIC is a highly effective, non-toxic, anti-inflammatory agent useful for the treatment of MS, as well as for the treatment of EAE, an animal model directly analogous to MS. The response in BBI/BBIC treated rats with EAE is similar to the earlier demonstrated response in BBI/BBIC treated rats with EAN. The method is also highly effective for the treatment of other chronic inflammatory autoimmune diseases, such as rheumatoid arthritis, and chronic neuroinflammatory diseases, such as GBS, although the invention is not to be limited to only the identified examples.

In preferred embodiments of the invention, as set forth by Example, BBI/BBIC produced according to known methods effectively suppresses inflammation, such as that which is found associated with rheumatoid arthritis, and in particular effectively suppresses neuroinflammation of the type characteristically found in autoimmune diseases, including MS and GBS. The clinical study set forth in Example 3 is intended to exemplify the parameters of the method of using BBI/BBIC to reduce, inhibit, suppress or prevent inflammation, preferably neuroinflammation in a patient with MS, GBS or rheumatoid arthritis. However, the parameters set forth therein are intended to be exemplary, not limiting as to the dosage or treatment regime that may be used in accordance with the present methods.

By "reduce," "inhibit," "suppress" or "prevent" the chronic inflammation or neuroinflammation is meant to modulate the inflammatory or neuroinflammatory effect of the disease in a patient or animal subject affected by the disease, as compared with a matched, untreated control patient or subject when an effective amount of the BBI/BBIC is administered, such that the inflammation or neuroinflammation is measurably or visibly changed (e.g, reduced, inhibited, suppressed or prevented, as such terms are commonly understood).

In the present invention, compositions comprising BBI for the treatment of diseases or a typical inflammatory conditions are also provided, particularly for neuroinflammatory conditions involved in autoimmune disease. MS and GBS are, as previously noted, reported to be autoimmune diseases or disorders. Other such autoimmune diseases characterized by inflammation include, but are not limited to, e.g., systemic lupus erythematosis and myasthenia graves. However, in the event that MS or GBS are shown not to be autoimmune in nature, the principles set for herein for their treatment remain unchanged. In a preferred embodiment, the BBI/BBIC compositions further comprise a pharmaceutically acceptable carrier.

By "BBI" it is meant any Bowman-Birk Inhibitor or Bowman-Birk Inhibitor product, including, but not limited to, BBI prepared by methods known in the art and BBI concentrates ("BBIC") prepared in accordance with the method of U.S. Pat. No. 5,217,717. Also provided are methods of treating inflammation, particularly neuroinflammation, in an animal by administering an effective amount of a composition comprising BBI.

By "animal" is meant, but is not limited to, any mammal including humans. In the alternative, the term "patient" is also used to indicate the animal, mammal or human being treated with BBI/BBIC in accordance with the disclosure of the present invention. When animal models are treated by the present method, the term "subject" is more frequently used, rather than "patient."

It is clear from many animal studies that orally ingested BBI is absorbed and has systemic effects (reviewed in Kennedy, 1998). The structure of the BBI molecule is extremely stable, such that it survives the digestive process and appears in the colon, etc., as an intact protease inhibitor capable of inhibiting proteolytic activities (Yavelow et al., *Cancer Res.* 43:2454-2459 (1983); Billings et al., *Canc. Lett.* 62:191-197 (1992)). Many other protease inhibitors which have been studied in vivo do not survive the digestive process. Moreover, when BBI reaches the colon in intact, active form after ingestion, approximately half of ingested BBI is taken up into the bloodstream (Billings et al., 1992).

The amount of BBI taken up from the gastrointestinal tract into the blood and distributed to internal organs is such that biological effects from BBI are expected in many different organ systems. Absorbed BBI is measurable in humans (e.g., U.S. Pat. No. 5,961,980).

Antibodies to "reduced BBI" have been produced and utilized to measure blood and urine levels of BBI after the ingestion of BBIC (Wan et al., *J. Immunol. Meth.* 180:117-130 (1995); U.S. Pat. Nos. 5,616,492 and 5,618,679). Pharmacokinetic studies utilizing these antibodies have been performed in rodents, dogs and humans (Wan et al., unpublished data). It is also clear that BBI can be internalized by intestinal epithelial cells (Billings et al., *Eur. J. Canc.* 27:903-908 (1991)).

It is further known that dietary concentrations of BBIC/BBI capable of preventing cancer in animals in many different organ systems are not toxic. Yet, these same concentrations of BBI/BBIC are known to affect inflammation in animals (Kennedy, 1993A; Kennedy, 1998; Kennedy, *Preventive Med.* 22:796-811 (1993C); Kennedy, *Cancer Res.* (suppl) 54:1999s-2005s (1994); Kennedy, In *Nutrients in Cancer Prevention and Treatment*, Prasad (ed) 1995B, pp. 71-82).

Compared to raw soybeans, the trypsin inhibitory activity of BBIC has been greatly reduced and the chymotrypsin inhibitory activity has been increased (Kennedy, 1993B). It was, however, earlier thought that the soybean-derived protease inhibitors had the potential to inhibit the growth of young animals, and, perhaps, contribute to pancreatic cancer development in rats. However, it is now recognized by many investigators that the soybean protease inhibitors are not responsible for the growth suppressing effects of raw soybean products in young animals (Birk, In *Protease Inhibitors as Cancer Chemopreventive Agents*. Troll W, Kennedy A R (eds). New York, Plenum Press, 1993, pp. 97-106). When BBIC was tested at doses considerably higher than the doses of BBIC typically administered to people, significant drug induced toxicity was not observed in any organ, including the pancreas, in at least three species of animals (mice, rat, hamsters) evaluated in the Kennedy laboratory (e.g., Kennedy, 1993A), and in sub-chronic and chronic toxicity studies performed in animals (rodents, dogs) and studied at Southern Research Institute (SR1) and MPI Research, Inc. (Page et al., unpublished data (Page et al., SRI-CBE-94-135-7482 and SRI-CBE-94-060-7482, Birmingham, Ala.; Southern Research Institute, 1994; Serota, 560-057 and 560-058, MPI Research, Inc., Mattawan, MI (2000)).

Animal experiments at extremely high doses of BBIC have been carried out for as long as the animals' life spans. Thus, even at extremely high doses of dietary BBIC, no histopathologic alterations in the pancreas have been observed. Consequently, the assumption that the soybean protease inhibitors are involved in rat pancreatic cancer development is erroneous, as discussed extensively in, e.g., Kennedy, 1993A-C; Kennedy, 1994; Kennedy, *J. Nutr.* 125: 733s-743s (1995C)). In human trials, no adverse effects of BBIC on the pancreas have been observed.

The possibility that soybean protease inhibitors may have impact upon the growth of the rat pancreas is triggered by the ability of the protease inhibitors to inhibit trypsin, but not chymotrypsin (Birk, 1985; Birk, 1975), while the ability to inhibit carcinogenesis, and presumably inflammation, is associated with the ability to inhibit chymotrypsin (which is why the strength of BBIC doses is measured in CI units) (Yavelow et al., 1985; Kennedy 1993B). However, the two protease inhibitor sites in BBI are separable and distant from each other in the molecule.

Although presently available in concentrates extracted from soybeans, BBI is also found in other members of the legume family of plants, such as adzuki beans, black beans, black-eyed peas, peas, lima beans, kidney beans, navy/white beans, pinto beans, chick peas, peanuts, lentils and the like. Using the methods known in the prior art for preparing the enriched BBIC concentrates from soybeans, one of ordinary skill in the art could readily prepare BBI concentrates from other legumes. Although the resulting concentrates may not have the same CI values as soybean BBIC, the key factor is that there is some degree of chymotrypsin inhibition. Thus, the resulting concentrate would be quantifiable in CI units.

On a comparable weight basis, the doses of soybean BBIC needed to prevent cancer development or have an anti-inflammatory effect, are well below the doses of soybean protease inhibitor activity associated with triggering the feedback response leading to pancreatic abnormalities (Kennedy, 1993A-C, Kennedy, 1994, Kennedy, 1995C). As a result, even on a theoretical basis, the doses of BBI/BBIC used in the treatment of MS would not create a toxicity problem in human patients.

The only toxicity which has previously been associated with BBI/BBIC treatment of animals has been that of causing toxicity to the developing embryo when injected at an extremely high level into pregnant mice (Kennedy, 1993A-C; Kennedy, 1994). At normal dosages, BBI/BBIC do not have teratogenic effects; in fact, these agents have been shown to prevent birth abnormalities, as has been reviewed by Kennedy, 1993A-C and Kennedy, 1994. No toxicity due to BBIC has been reported in any human trial in which BBIC has been used. Nevertheless, although deleterious effects were not expected from the use of dietary BBI/BBIC, early human clinical trials with BBIC are limited to post-menopausal females so that potential problems for a developing embryo can not occur.

In a dose-ranging trial of BBIC in humans with benign prostatic hyperplasia for a 6 month period, there were found to be no increased adverse symptoms or abnormalities in standard laboratory assays when compared to placebo administration for the same time period (Malkowicz, et al., *The Prostate* 48:16-28, (2001); see also following Tables 1 and 2 listing toxicity study findings). The highest BBIC dose given was 400 CI units twice daily, which is the same as that of the present invention. Accordingly, no toxicity issues are expected in the treatment of humans with BBIC for MS or other inflammatory autoimmune diseases.

TABLE 1

Toxicities: in Treated Patients

| Outcome | N | Maximum Toxicity Score | | | | |
|---|---|---|---|---|---|---|
| | | 0 | 1 | 2 | 3 | 4 |
| WBC | 14 | 12 (86%) | 2 (14%) | 0 | 0 | 0 |
| Hemogloblin | 14 | 12 (86%) | 2 (14%) | 0 | 0 | 0 |
| Hematocrit | 14 | 13 (93%) | 1 (7%) | 0 | 0 | 0 |
| Platelet | 14 | 13 (79%) | 1 (7%) | 0 | 0 | 0 |
| Granulocytes a | 7 | 6 (86%) | 1 (14%) | 0 | 0 | 0 |
| Lynphocytes | 14 | 9 (64%) | 5 (36%) | 0 | 0 | 0 |
| Mononuclear Cells ab | 6 | 4 (67%) | 2 (33%) | 0 | 0 | 0 |
| Eosinophils | 14 | 13 (93%) | 1 (7%) | 0 | 0 | 0 |
| Basophils | 14 | 13 (93%) | 1 (7%) | 0 | 0 | 0 |
| Calcium | 14 | 14 (100%) | 0 | 0 | 0 | 0 |
| Lipase | 14 | 11 (79%) | 2 (14%) | 1 (7%) | 0 | 0 |
| Amylase | 14 | 12 (86%) | 1 (7%) | 1 (7%) | 0 | 0 |
| Sodium | 14 | 10 (71%) | 4 (29%) | 0 | 0 | 0 |
| Potassium | 14 | 12 (86%) | 2 (14%) | 0 | 0 | 0 |
| Chloride | 14 | 11 (79%) | 3 (21%) | 0 | 0 | 0 |
| Carbon Dioxide | 14 | 11 (79%) | 3 (21%) | 0 | 0 | 0 |
| Urea/Nitrogen | 14 | 11 (79%) | 3 (21%) | 0 | 0 | 0 |
| Creatinine | 14 | 12 (86%) | 2 (14%) | 0 | 0 | 0 |
| Total Bilirubin | 14 | 13 (93%) | 1 (7%) | 0 | 0 | 0 |
| ALT | 14 | 10 (710/,) | 4 (29%) | 0 | 0 | 0 |
| AST | 14 | 14 (100%) | 0 | 0 | 0 | 0 |
| Alkaline Phosphatase | 14 | 14 (100%) | 0 | 0 | 0 | 0 | a - These measurements were not taken for Arizona patients.
b - One patient had mononuclear cell measurements at baseline only.

TABLE 2

Toxicities in Control Patients (N = 4)

| Outcome | Maximum Toxicity Score | | | | |
|---|---|---|---|---|---|
| | 0 | 1 | 2 | 3 | 4 |
| WBC | 4 | 0 | 0 | 0 | 0 |
| Hemogloblin | 4 | 0 | 0 | 0 | 0 |
| Hematocrit | 4 | 0 | 0 | 0 | 0 |
| Platelet | 3 | 1 | 0 | 0 | 0 |
| Granulocytes a | 2 | 0 | 0 | 0 | 0 |
| Lynphocytes | 2 | 2 | 0 | 0 | 0 |
| Mononuclear Cells ab | 2 | 0 | 0 | 0 | 0 |
| Eosinophils | 4 | 0 | 0 | 0 | 0 |
| Basophils | 4 | 0 | 0 | 0 | 0 |

TABLE 2-continued

Toxicities in Control Patients (N = 4)

| Outcome | Maximum Toxicity Score | | | | |
|---|---|---|---|---|---|
| | 0 | 1 | 2 | 3 | 4 |
| Calcium | 4 | 0 | 0 | 0 | 0 |
| Lipase | 4 | 0 | 0 | 0 | 0 |
| Amylase | 3 | 1 | 0 | 0 | 0 |
| Sodium | 4 | 0 | 0 | 0 | 0 |
| Potassium | 3 | 1 | 0 | 0 | 0 |
| Chloride | 3 | 1 | 0 | 0 | 0 |
| Carbon Dioxide | 2 | 2 | 0 | 0 | 0 |
| Urea/Nitrogen | 3 | 1 | 0 | 0 | 0 |
| Creatinine | 3 | 1 | 0 | 0 | 0 |
| Total Bilirubin | 4 | 0 | 0 | 0 | 0 |
| ALT | 2 | 2 | 0 | 0 | 0 |
| AST | 4 | 0 | 0 | 0 | 0 |
| Alkaline Phosphatase | 4 | 0 | 0 | 0 | 0 | a - These measurements were not taken for Arizona Patients.

Administration of an effective amount of the claimed compositions, either as a prophylactic dietary supplement or a pharmaceutical, is within the teachings of the invention. The term "effective amount" refers to an amount which alters the expression of certain types of proteolytic activities. Such an amount can be determined by those of skill in the art in accordance with known methods. For example, based on information determined in the accompanying Example, the preferred dose is 300-3000 mg/day, more preferably 400-1000 mg/day, most preferably about 800 mg/day. However, doses in the range of 200-4000 mg/day are effective in humans (50-100 μg/ml X 4000 ml (average blood volume in man)=200-400 mg BBIC; (100-400 CI units of BBIC is equivalent to 1000-4000 mg BBIC, as described in Kennedy, *Prevent. Med.* 22:796-811, pp. 797 (1993D)). Optimal dosage may vary by body weight.

Further, based on data from the published literature, doses of purified BBI as low as 1.3 mg/day (in rats) and more than 150 mg/day are effective in animal models of carcinogenesis (St. Clair et al., *Cancer Res.* 50:580-586 (1990); Kennedy, 1995C; van Hofe et al., *Carcinogenesis* 12:2147-2150 (1991)). Doses lower than 1 mg/day to rats are likely to be effective as well (Kennedy, *J. Cell. Biochem.* 22:188-194 (1995D)), with doses of as little as 0.001 .mu.g/ml showing activity in vitro to suppress the malignant transformation of irradiated cells (Yavelow et al., 1985). Such in vitro results would suggest that doses considerably lower than human doses of 2000 mg (2000 mg BBIC=200 CI units) BBIC per day might be effective in the treatment of inflammation.

Compositions of the present invention may be administered parenterally, rectally, topically, transdermally or orally. However, the preferred administration is oral. Administration as either a prophylactic dietary supplement or as a pharmaceutical are contemplated. Published studies have shown that BBI is effective following a variety of routes of administration, including oral dosing (Kennedy, 1995C; Evans et al., *Radiat. Res.* 132:259-262 (1992)). Examples of pharmaceutical or prophylactic dietary supplement formulations include, but are not limited to, syrups, suspensions, emulsions, tablets, capsules, lozenges and mouthwashes.

One embodiment of the invention is a liquid formulation comprising a suspension or solution of the composition in a pharmaceutically acceptable liquid carrier. Suitable liquid carriers include, but are not limited to, ethanol, glycerin, non-aqueous solvents such as polyethylene glycols, oils or water with a suspending agent, preservatives, flavorings or coloring agents, or any suitable combination thereof.

In another embodiment, a composition in the form of a tablet is prepared using any suitable pharmaceutical carrier routinely used for preparing solid formulations. Examples of such carriers include, but are not limited to, magnesium stearate, starch, lactose, sucrose and cellulose. Pharmaceutically acceptable fillers and supplements may also be added.

Compositions in the form of capsules are prepared using routine encapsulating procedure. For example, pellets, granules or powder containing a composition of the instant invention can be prepared using standard carriers and then filled into a hard gelatin capsule. Alternately, a dispersion or suspension can be prepared using any suitable pharmaceutical carrier(s), and the dispersion or suspension is then filled into a soft gelatin capsule. Suitable pharmaceutical carriers include, but are not limited to, aqueous gums, cellulose, silicates and oils.

In yet another embodiment, a composition for parenteral administration is formulated as a solution or suspension. This solution or suspension will generally include the composition of the instant invention in a sterile aqueous carrier or parenterally acceptable oil. Examples of parenterally acceptable oils include, but are not limited to, polyethylene glycol, polyvinyl pyrrolidone, lecithin, arachis oils and sesame oil. Alternatively, the solution can be lyophilized and then reconstituted with a suitable solvent just prior to administration.

In addition, the BBI/BBIC composition is administered to the patient in conjunction with other drugs, medicaments, treatments or therapies to achieve reduction, suppression, inhibition or elimination of inflammation in the patient suffering from an inflammatory autoimmune disease, particularly a neuroinflammatory disease.

The invention is further described by example. The examples, however, are provided for purposes of illustration to those skilled in the art, and are not intended to be limiting. Moreover, the examples are not to be construed as limiting the scope of the appended claims. Thus, the invention should in no way be construed as being limited to the following examples, but rather, should be construed to encompass any and all variations which become evident as a result of the teaching provided herein.

EXAMPLES

Although the certain of the disclosed examples were conducted using recognized animal models to allow for the detailed in vivo evaluation of the therapy, the findings are directly applicable to human neuroinflammatory autoimmune disease, particularly MS, Guillain Barre Syndrome and rheumatoid arthritis, and provide the foundation for additional studies in to the nature of the inflammatory response in humans.

Example 1

BBIC Inhibits Experimental Allergic Neuritis (EAN) in Rats

EAN was induced in seven week old Lewis rats using a synthetic peptide (SP26) corresponding to amino acid residues 53-78 of bovine myelin P2 protein. A solution of peptide in normal saline was emulsified with Complete Freund's Adjuvant (CFA) in a 1:1 proportion and injected into the hind footpads. A total of 150 µg peptide and 100 µl of CFA was injected into each rat. A total of ten rats were injected. Of the ten animals, five (5) of the rats were also given 200 mg of BBIC in normal saline orally the first five days of every week. The remaining five (5) control rats were given saline only, without BBIC.

The rats were observed and clinically scored daily according to the following criteria, with half points used for intermediate signs: 0=normal; 1=flaccid tail; 2=flaccid tail, plus inability to spread toes; 3=paraplegia; 4=quadriplegia; 5=death (Rostami et al., 1990).

The results of this study were striking. The BBIC-treated rats showed clinical signs of EAN for only 12 days; whereas the control rats showed clinical signs of EAN for 27 days, and remained symptomatic at the conclusion of the experiment. In both the control animals and the BBIC-treated animals, the peak in disease severity was manifested on day 17 post immunization (pi.). At the peak of the disease, the clinical scores of the 5 control rats averaged about 3 (paraplegia, hindlimb paralysis), while the scores of the 5 BBIC-treated rats averaged less than 1 (flaccid tail). In other words, the animals given BBIC were walking on all four limbs, while the control animals were dragging their paralyzed hindlimbs.

Example 2

Inhibition of EAN by Soybean Bowman Birk Protease Inhibitor

To further understand the unique properties of BBIC as therapeutic treatment that can substantially decrease or even completely block the clinical signs of EAN, the following experiment was conducted. The inhibition was shown to be associated with the induction of apoptosis of $CD4^+$ T lymphocytes, resulting in the absence of effector cells in the EAN lesions, followed by the subsequent amelioration of the disease.

Materials and Methods

Animals. Female Lewis rats (n=12, Charles River, Raleigh, N.C.), weighing 140-150 (g), were immunized with 150 µg of SP26 as reported previously (Rostami et al., 1990). Rats were observed daily for body weight change and clinical signs of EAN, which were scored as in Example 1.

BBIC treatment. Treatment was started on day 1 post immunization (pi.) and terminated at day 20 pi. For each experiment a group of rats (n=6) was provided with BBIC (Pharmacia Leo Therapeutics, Helsinborg, Sweden). Rats were giving 500 mg/ml of BBIC, in drinking water, every day on a regular basis. PBS-treated EAN rats were used as a control as described in Example 1. Following BBIC treatment, disease severity was scored according to the above-described scale (mean±SD; n=6) for each group at each time point.

Tissue preparation. Rats were sacrificed at days 0, 7, 10, 13, 17, 20, and 24 pi. Quickly harvested cauda equina (CE), from which the fragments of spinal cords had been carefully excluded, and sciatic nerves (SN) were rapidly frozen in isopentane precooled in liquid nitrogen, and stored at −70° C.

Histopathological evaluation. Sections of CE and SN obtained from treated and untreated rats (PBS control) were stained with hematoxilin/eosin to identify mononuclear infiltrates. Areas of demyelination were identified in sections stained with luxol fast blue. Sections were evaluated and graded using the following scale: 0=normal perivascular area; 1=mild cellular infiltrate adjacent to a vessel; 2=cellular infiltrate plus demyelinated fibers adjacent to a blood vessel and in the immediate surroundings; 3=cellular infiltrate and demyelinated fibers around the vessels, confluence with infiltrates from more distant vessels.

Cell preparation. Rats were sacrificed at day 13-pi., and perfused with 150 ml of ice-cooled PBS via left ventricle. Spleens were removed and pooled in ice-cooled RPMI-1640 (Life Technologies, Gaithersburg, Md.) containing 2% fetal calf serum (FCS) (Sigma, St. Louis, Mo.). A single cell suspension was obtained from spleens by pressing them through a 70 μm Falcon cell strainer 2350 (Becton Dickinson, San Jose, Calif.). Erythrocytes in suspension were lysed by Tris-buffered ammonium chloride. Thioglycollate-elicited peritoneal macrophages ("elicited macrophages") were isolated 4 days later, after intraperitoneal stimulation of the rats with 20 ml of thioglycollate medium, and suspended in complete RPMI 1640 supplemented with 10% FBS, at $10^6$ cells/ml. Elicited macrophages were comprised of 85-90% typical mononuclear phagocytes. All isolated cells were counted, after which cell viability was determined by trypan blue exclusion and found to be >95%.

Proliferation assay. The proliferation response of the splenocytes was examined by $^3$H-thymidine incorporation. Briefly, 200 μl of splenocyte suspension ($10^6$ cells/ml) were incubated in 96-well polystyrene microtiter plates (Nunc, Roskilde, Denmark) at 37° C. in a 5% $CO_2$ incubator, with or without SP26 (50 μg/ml) in the presence or absence of BBIC (500 μg/ml). After 60 hours, cells were pulsed with by $^3$H-thymidine (1 μCi/well; Amersham) for 12 hours. Cells were harvested and $^3$H-thymidine incorporation was measured in a liquid β-scintillation counter.

Immunostaining and FACS analysis. Fluorescein (FITC)-labeled anti-rat CD3 (mouse $IgG_3$, G4.18 clone), CD4 (mouse $IgG_{2a}$, OX-35), CD8 (mouse $IgG_1$, OX-8), and rat macrophages (anti-EDI mouse $IgG_1$, k: 1C7) monoclonal antibodies, and phycoerythrin (PE)-labeled anti-rat CD3, CD4, CD8, CD25 (mouse $IgG_{2a}$, OX-39) and NKR-P1A (mouse $IgG_1$, 10/78) monoclonal antibodies were purchased from PharMingen, San Diego, Calif. FITC-labeled anti-rat CD11b (mouse $IgG_{2a}$, OX-42) and CD25 monoclonal antibodies, PE-labeled anti-rat CD11b and B cells (mouse $IgG_{2a}$, RLN-9D3) monoclonal antibodies were purchased from Caltag Laboratories, Burlingame, Calif. One million ($10^6$) cells were stained in 5 ml FACS tubes by 1 μg of each monoclonal antibody following standard protocol (PharMingen). Labeled cells were analyzed by FACScan (Becton Dickinson) operated by CellQuest software (Becton Dickinson).

Detection of apoptosis. Apoptosis was determined using Flurescein Apoptosis Detection System Kit (Promega, Madison, Wis.). At day 13 pi., splenocytes from normal or EAN rats were obtained and cultured with BBIC (500 μg/ml), SP26 (50 ng/ml), or combinations thereof, for 72 hours. Cell suspensions were fixed with 4% paraformaldehyde for 30 minutes at room temperature and then permeabilized with 0.1% Triton X-100 in 0.1% sodium citrate for 2 minutes on ice. TUNEL reaction mixture (50 μl) was added to samples incubated in a humidified chamber for 60 minutes at 37° C. in the dark. Cell suspensions were then incubated with propidium iodide (PI) (Sigma). The cells were analyzed as above, by FACScan operated by CellQuest software.

Cytokine enzyme-linked immunosorbent assays (ELISAs). IL4 and IFNγ were assayed by ELISAs developed by the researcher's laboratory. The lower and upper ranges for this assay were from 0.039 to 2.5 ng/ml, respectively. IFNγ determinations covered a range from 0.02 to 2.0 ng/ml. An IL-10 assay was performed in accordance with manufacturer's recommendations (Endogen, Inc. Woburn, Mass.). Data were expressed as the mean cytokine concentration per ml from replicate determinations ±SEM.

Measurement of nitrite. Nitrite (NO) was assayed by measuring the end product nitrite, which was determined by a colorimeter assay based on the Griess reaction. Aliquots of cell culture supernatants (100 μl) were mixed with 100 μl of Greiss reagent at room temperature for 10 minutes. The absorbance was measured at 540 nm in an automated plate reader. The concentration of nitrite was determined by reference to a standard curve of sodium nitrite (Sigma).

Statistics. Data were analyzed by using the Student's t-test, wherein P<0.05 indicated that the value of the test sample was significantly different from that of the control level.

Results

Effects of BBIC on the Clinical Course and Histological Signs of EAN.

BBIC treatment in vivo ameliorates the clinical course of active EAN. All animals immunized with SP26 developed flaccid, ascending paralysis starting from the tail at day 11-12 pi. The disease reached its peak at day 16 pi., then recovery started (FIG. 1, control). Rats recovered clinically by about day 30 pi. with mild sequele. The mean duration of the disease was 23±2.6 days, with a mean score of 3.0±0.25. Rats immunized with CFA plus PBS without SP26 showed no clinical signs of disease (data not shown).

To determine whether oral BBIC could modify the clinical course of active EAN, the treatment was started on day 1 pi., and terminated at day 20 pi. (FIG. 1, BBIC). Rats (groups of 6) were giving 500 mg/ml of BBIC, in drinking water, every day on a regular basis. Matched rats that received only PBS were used as a control. Following BBIC treatment, disease severity was scored according to the above-described scale (mean±SD; n=6 for each group at each time point).

As shown in FIG. 1, the data indicated that treatment with BBIC dramatically decreased clinical severity and pathologic expression of EAN in Lewis rats injected with the neuritogenic SP26 peptide when compared to that in animals fed the PBS diluent without BBIC. There was also significantly reduced inflammatory cell accumulation in the peripheral nerve tissue of BBIC-treated animals. Some evidence also suggested increased frequency of lymphocyte apoptosis in BBIC-treated animals (FIG. 2)

BBIC treatment in vitro ameliorates clinical course of passive EAN. To determine whether BBIC could modify the clinical course of passive EAN, the disease was induced by the adoptive transfer of $10^7$ SP26-specific splenocytes, treated or untreated by BBIC in vitro for 72 hours before transfer. Following transfer, disease severity was scored according to the above-described scale (mean±SD; n=6 for each group at each time point). On day 15 pi passive EAN/BBIC-untreated and passive EAN/BBIC-pretreated animals were sacrificed and staining was performed.

Figure 2:
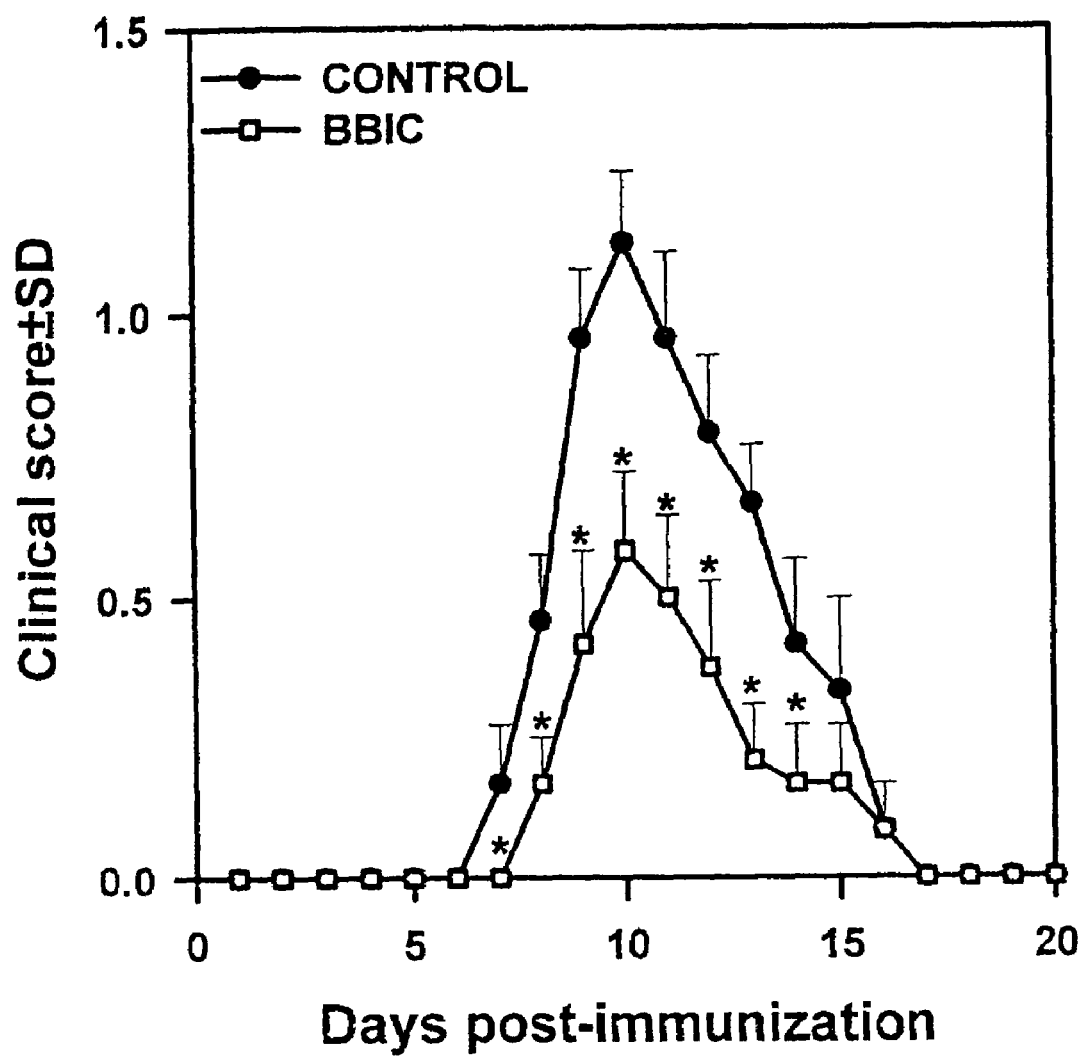
FIG. 2 graphically depicts the effect of pretreatment with BBIC to ameliorate the clinical course of passive EAN. Disease severity was scored according to the above-described scale (mean±SD; n=6 for each group at each time point). The representative experiment of six separate experiments is shown.

As shown in FIG. 2, treatment by BBIC in vitro, but not in vivo, following cell transfer, significantly decreased clinical severity (inflammation) of passive EAN (P<0.05). A large number of cell infiltrates were observed in sections of CE and SN isolated either from EAN PBS- or BBIC-in vivo-treated animals (data not shown).

Potential Pathways Involved in BBIC Action.

Figure 3:
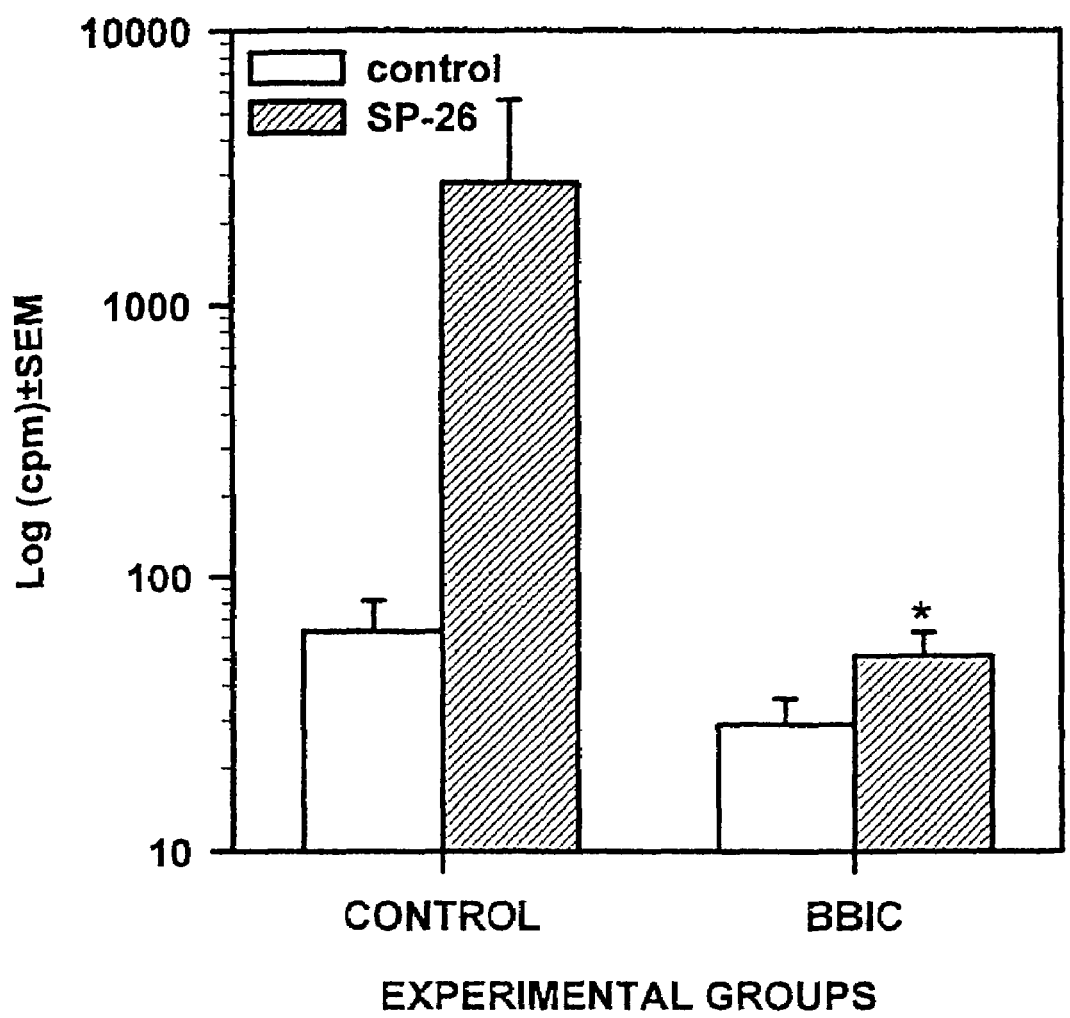
FIG. 3 graphically depicts BBIC inhibition of antigen-specific proliferation. Splenocytes, isolated from EAN animals and incubated with or without SP26 in the presence or absence of BBIC, were pulsed with $^3$H-thymidine and the $^3$H-thymidine incorporation is shown. Values were significantly different (p<0.05) from proliferation values of cells untreated by SP26, and significantly different (p<0.05) from splenocytes stimulated with SP26. The data are representative of ten (10) experiments. Mean±SD; n=6 is shown.

(i) Inhibition of antigen-specific proliferation by BBIC in vitro. As shown in FIG. 3, when splenocytes isolated from EAN animals (day 13 pi.) were incubated with or without SP26 in the presence or absence of BBIC, cellular proliferation was significantly enhanced in the presence of SP26

(significantly more $^3$H-thymidine was incorporated). By comparison, the proliferation of splenocytes incubated in culture media alone (without SP26) was not augmented. However, when the splenocytes were cultured with BBIC, cells proliferation was significantly decreased in the presence of SP26, and not affected in the resting cell population.

(ii) Effects of the BBIC treatment on expression of CD3, CD4, CD8, CD11b, and ED-1.

Figure 4:
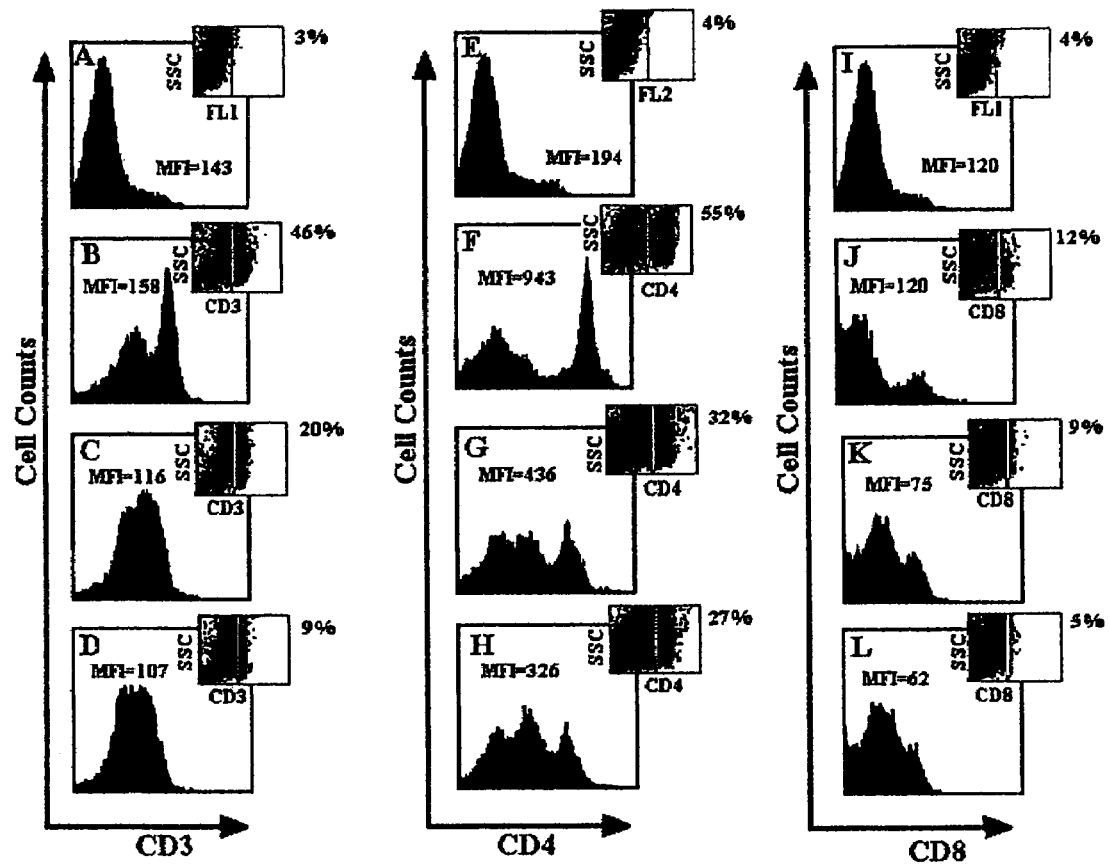
FIGS. 4A-4L graphically depict a series of FACS analyses of CD3, CD4, and CD8 expression following BBIC treatment in vitro.
Figure 5:
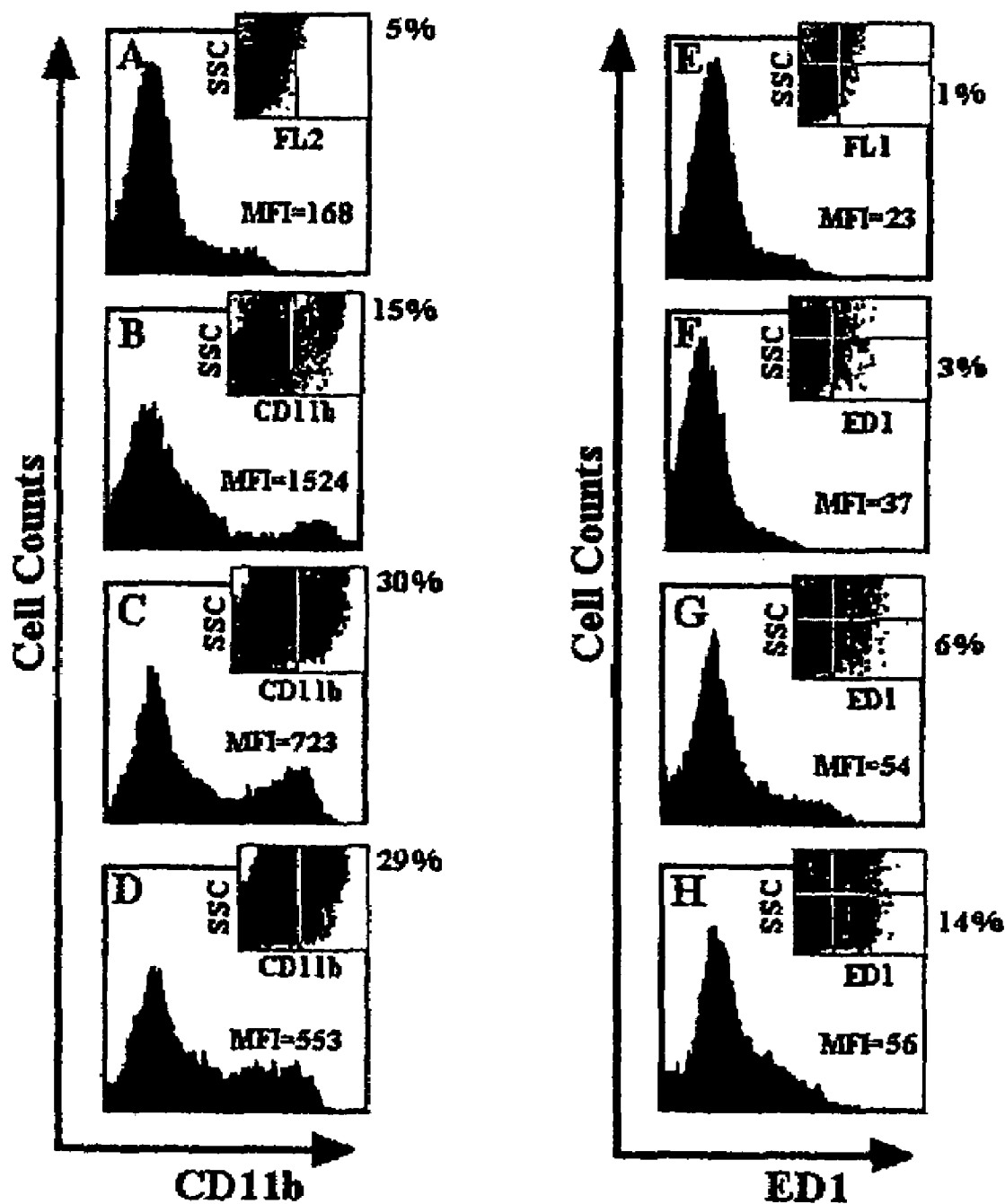
FIGS. 5A-5H graphically depict the increase in macrophage population after exposure to BBIC.

To characterize the influence of BBIC on T cell, B cell, NK cell and macrophage populations, cell debris was excluded from the data using forward and side light scatter plots (FIGS. 4 and 5), and cells were analyzed for $CD3^+$, $CD4^+$, and $CD8^+$ (T cells) (FIG. 4); $CD11b^+$ and $ED-1^+$ (macrophages) (FIG. 5); NKR-P1A$^+$ (NK cells); and pan-B markers. The data in FIG. 4 and FIG. 5 are representative of 6 different experiments.

The numbers in the figures refer to the mean fluorescence intensity (MFI), and the percentage of positive cells, plus they show that BBIC (FIG. 4, panels D, H, and L) down-regulated expression of CD3 (FIG. 4, panel D) and CD4 (FIG. 4, panel H) relative to expression by the cells analyzed after incubation in culture media (FIG. 4, panels B and F), or after treatment with SP26 alone (FIG. 4, panels C and G).

BBIC had no effect on CD8 (FIG. 4, panel L) or CD11b (FIG. 5, panel D) expression, but increased the expression of ED-1 from 3% (FIG. 5, panel F) to 14% (FIG. 5, panel H). Thus, it appears that BBIC treatment stimulated the macrophage population. The expression of NK and B cell markers, analyzed in the presence or absence of SP26, treated or untreated by BBIC, had no changes and was almost negligible (data not shown).

Figure 6:
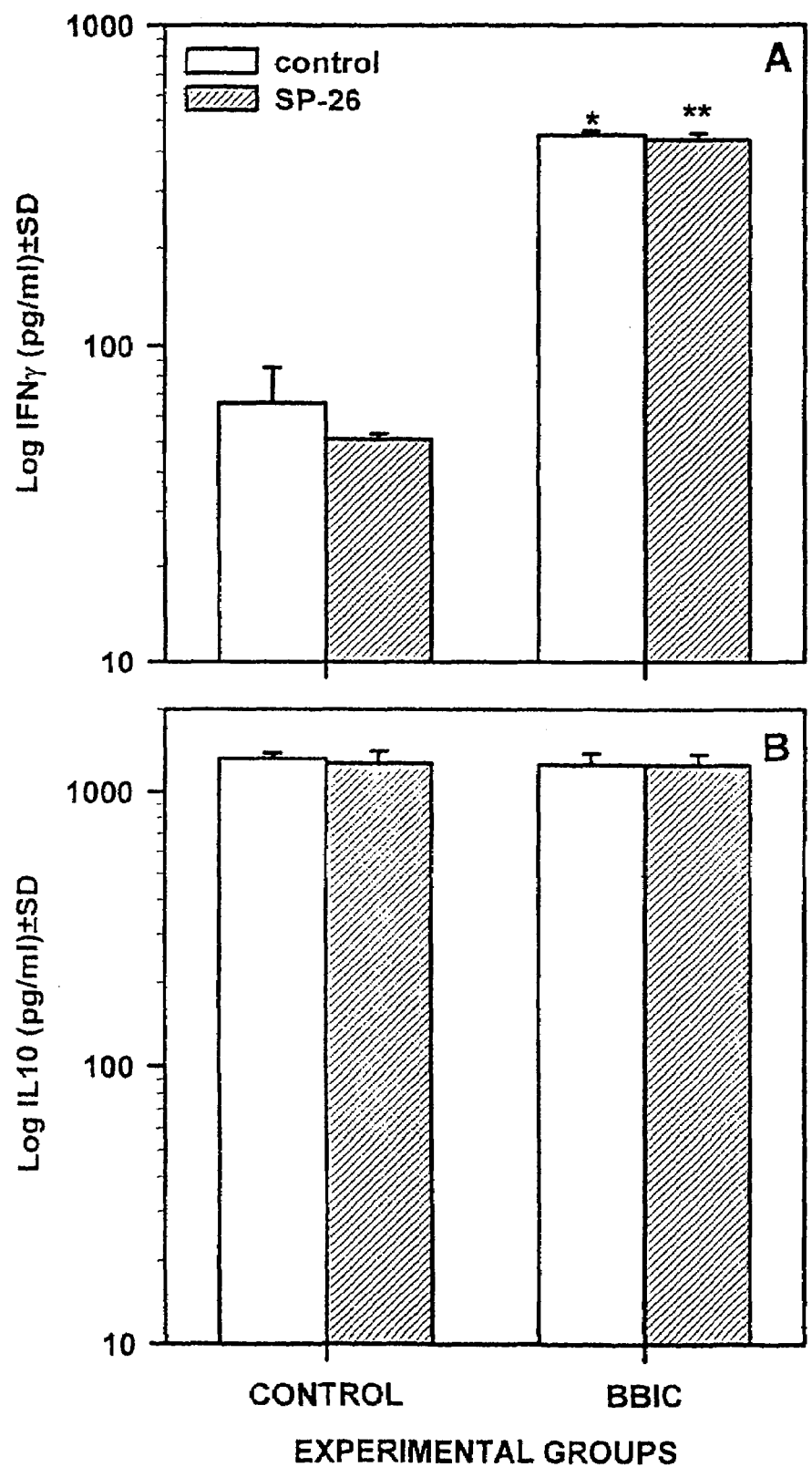
FIGS. 6A and 6B graphically depict amplification in response to BBIC treatment on the secretion of IFNγ (FIG. 6A), which had no effect on IL-10 production (FIG. 6B) from elicited macrophages isolated from EAN rats in response to SP26. Values were significantly different (p<0.05) from cytokine values of cells untreated by SP26, and significantly different (p<0.05) from macrophages stimulated with SP26. The data are the mean of six (6) experiments ±SEM (three replicates per experiment).

(iii) Influence of BBIC treatment on IFNγ, IL-10, IL-4, and NO release. Previous data indicated that macrophages can capture, process, and present antigens to T cells, and produce cytokines and mediators to participate in immune responses. To further elucidate the mechanisms involved in the suppression of EAN after BBIC administration, either elicited macrophages or splenocytes were obtained from PBS and BBIC-treated EAN rats at day 13 pi., and their activities were evaluated. Compared with PBS-treated rats, cells isolated from BBIC-treated rats showed higher secreted levels of IFNγ, both spontaneously and upon stimulation with SP26 (data not shown). Treatment by BBIC further augmented IFNγ release (FIG. 6A). At the same time, it was found that IL-10 release was not increased, either in the presence or absence of SP26, treated or untreated by BBIC (FIG. 6B). In addition, IL-4 was not detected in the culture fluids, under any of the conditions used (data not shown).

Figure 7:
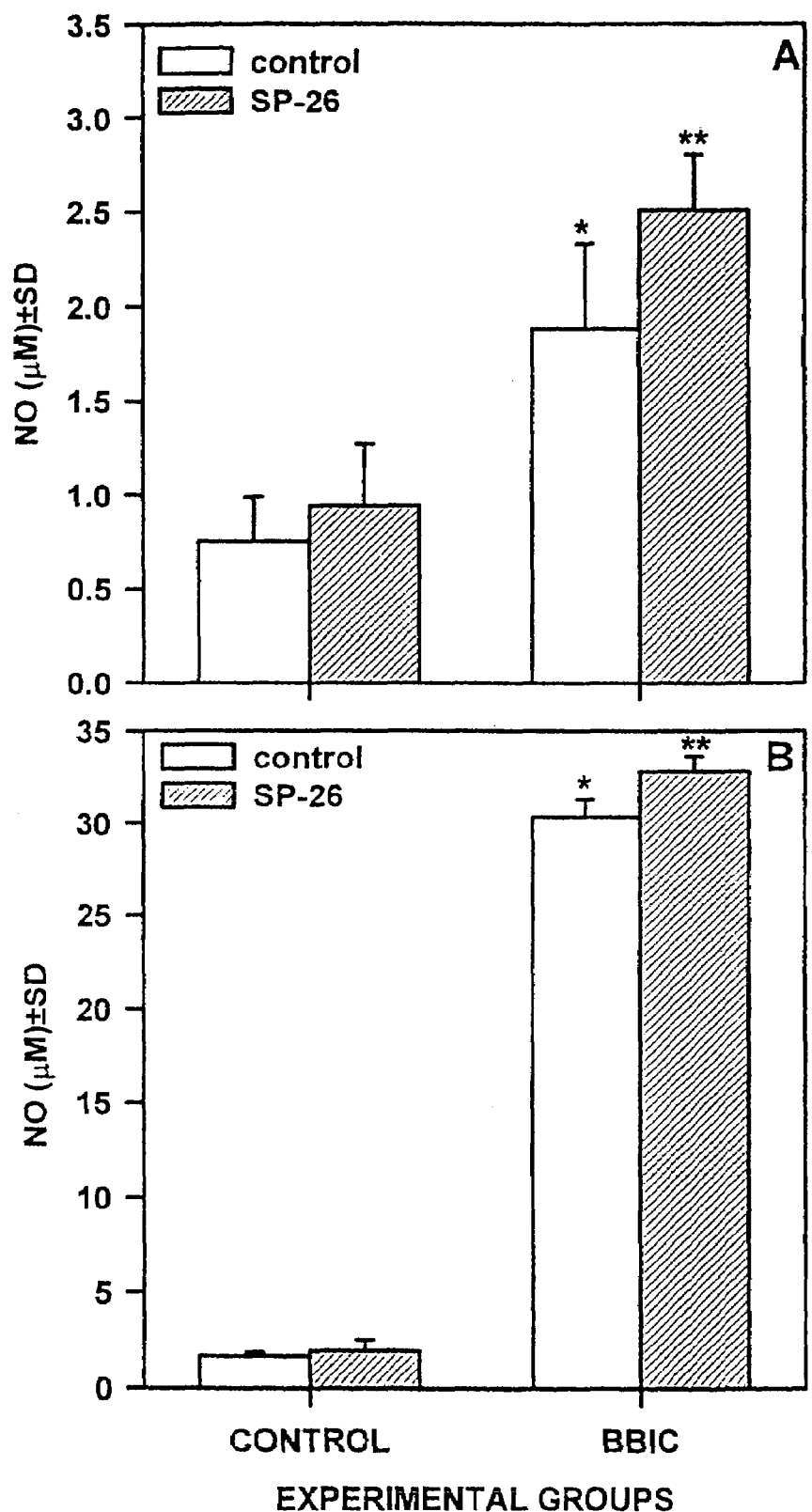
FIGS. 7A and 7B graphically depict the regulation of nitrite (NO) release by BBIC. Rat elicited macrophages, isolated from EAN animals and incubated with or without (control) BBIC in the presence or absence of SP26, were assayed for NO production after 4 hours (FIG. 7A) or 24 hours (FIG. 7B). Values were significantly different (p<0.01) from NO values of cells untreated by SP26, and significantly different (p<0.05) from macrophages stimulated with SP26. The data are the mean of four (4) experiments ±SEM (three replicates per experiment).

When macrophages were cultured with BBIC (500 μg/ml) for 4 hours (FIG. 7A) or 24 hours (FIG. 7B), nitrite production was dramatically augmented, suggesting that macrophage activation induced by BBIC treatment may increase IFNγ release, and consequently promote nitrite production by these cells.

(iv) Induction of differential cell apoptosis by BBIC in vitro. It has been reported that nitrite production is frequently associated with impaired T cell responses due to apoptosis and macrophage activation. Since the present results indicated that macrophage function are elevated by BBIC treatment, the apoptotic response was characterized for spleen cells isolated from EAN rats. On day 13 pi., splenocytes were obtained and incubated for 72 hours, with or without SP26, in the presence or absence of BBIC. Then, gated by size (FIG. 8, panel A), cells were analyzed by flow cytometry for an apoptotic response.

Figure 8:
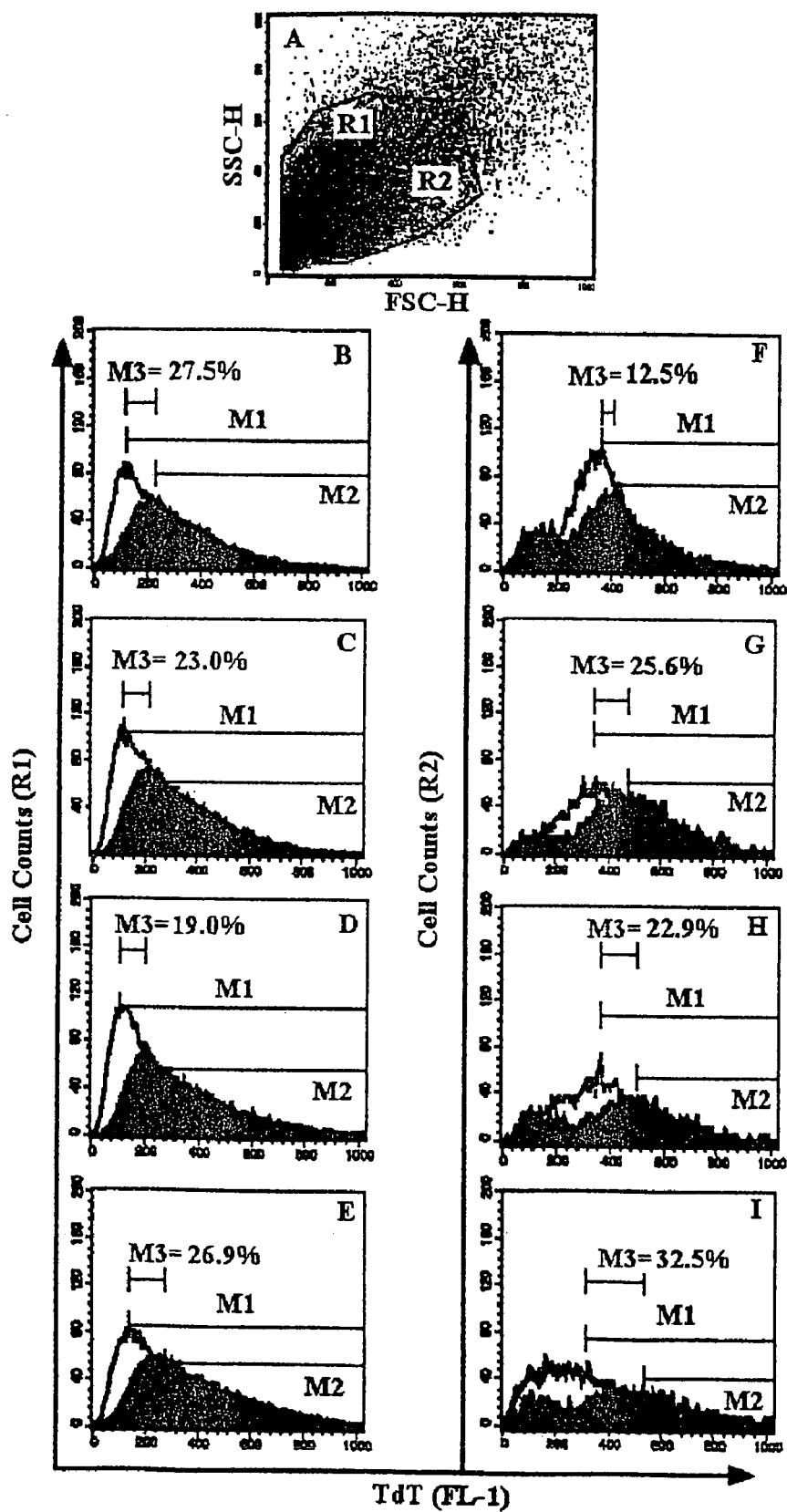
FIGS. 8A-8I graphically depict the differential apoptotic response induced by BBIC in vitro. Splenocytes isolated from EAN animals, were selected by the forward (FSC-H) and side (SSC-H) light scatters and gated by size (FIG. 8A).

In the absence of SP26 stimulation, the level of apoptosis was higher in the population of larger cells (27.5% (FIG. 8, panel B)) compared to relatively smaller cells (12.5% (FIG. 8, panel F)). This finding was explained by extrinsic effects, such as Fas/FasL-mediated apoptosis or cellular response to SP26 immunization. However, it was determined that upon in vitro stimulation with SP26, the R1 population (larger cells) was not affected after 72 hours of incubation in the presence or absence of BBIC (FIG. 8, panels C to E, respectively). In a co-culture of the R2 population (smaller cells) with a combination of SP26 and BBIC (FIG. 8, panel I), a much higher level of apoptosis (32.5%) was observed. This corresponded to the previously shown decrease in antigen-specific proliferation of splenocytes (FIG. 3), and to changes in $CD3^+$, $CD4^+$ expression (FIG. 4, panel D and panel K, respectively).

In sum, the immunomodulatory effects of BBIC on this experimental model of disease were associated with marked inhibition of antigen-specific proliferation and a decrease in CD3- and CD4-positive T cell subpopulations. Furthermore, treatment with BBIC substantially increased the number of macrophages, stimulated IFN-γ and nitrite release, and resulted in lymphocyte apoptosis. Accordingly, the apoptosis of lymphocytes induced by BBIC in the peripheral nervous system and lymphoid organs are directly associated with the absence of inflammatory cells in the EAN lesions and amelioration of the disease.

Example 3

Figure 9:
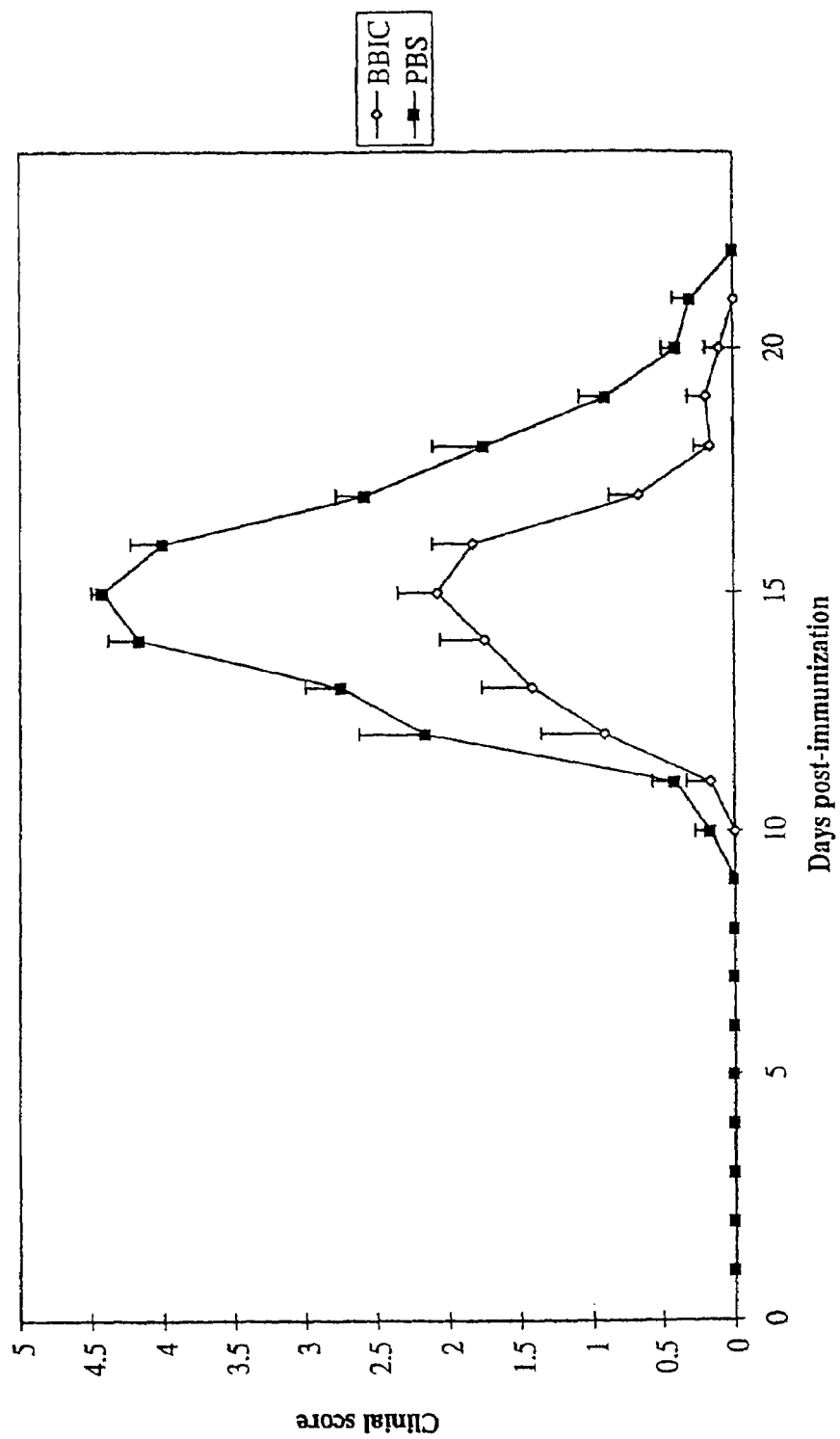
FIG. 9 graphically depicts the clinical effect of BBIC over time in the treatment of Lewis rats with EAE.
Figure 10:
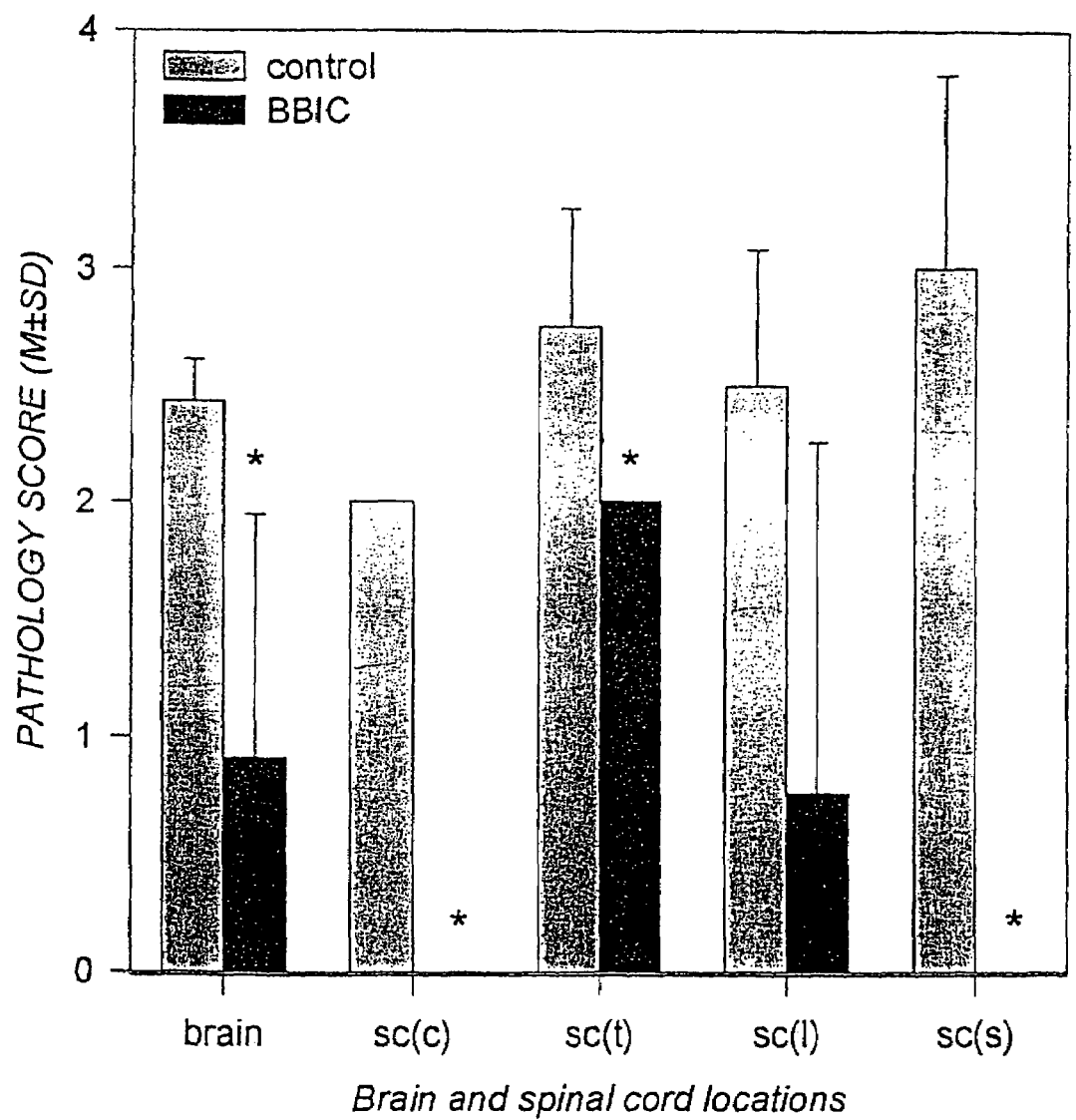
FIG. 10 graphically depicts the effect of BBIC for the treatment of Lewis rats with EAE, showing the difference in inflammatory demyelination in the CNS (brain and spinal cord) of BBIC-treated animals as compared with matching, untreated control animals. In the bar graph the first column provides data on the effect in "brain" tissue, while the remaining 4 columns provide data from various regions of the spinal cord ("sc"). Specifically. "sc(c)" refers to the cervical region of the spinal cord. "sc(t)" refers to the thoracic region of the spinal cord. "sc(l) refers to the lumbar region of the spinal cord, and "sc(s)" refers to the sacral region of the spinal cord. The asterisks (*) are used as noted above to show that there is a statistically significant change between the data from the untreated animals and the data from the matched treated animals.

Randomized, Double-Blind, Placebo-Controlled, Study of Safety, Tolerance and Clinical Effects of the Oral BBIC in Multiple Sclerosis In early studies, orally administered BBIC was seen to inhibit both the clinical and pathologic manifestations of EAE in Lewis rats inoculated with myelin basic protein (MBP) in complete Freund's adjuvant (FIGS. 9, 10). In light of this effect on EAE, a recognized and accepted animal model for human MS, a 1-year pilot study was planned to determine that oral administration of BBIC in the dose specified, is well-tolerated by patients with active MS, and to obtain a preliminary impression of the efficacy of BBIC treatment in halting the progression of relapsing-remitting MS. The results of the study will be quantified and correlated with effects determined in laboratory assays and brain assays. Analyses of blood and urine and brain MRIs will occur before BBIC therapy begins, and periodically during and after the BBIC therapy period. In addition, the level of markers of inflammation in blood are assessed. Any potential side effects of the BBIC treatment is closely monitored The clinical subjects consist of twenty individuals (ages 18-65) male and female, with well documented MS in a relapsing-remitting course are registered. Each patient must have exhibited at least one relapse during the year prior to initiation of the BBIC trial. These individuals are not receiving glatiramer or beta-interferon (INF-β), because of previously manifested side effects of these treatments or because the patient did not choose to receive glatiramer or INF-β.

All MS patients considered for this phase I study must be followed in the MS center of the Hospital of the University of Pennsylvania Medical Center. Eligibility for enrollment is based on independent examination by 2 staff physicians in the MS clinic using a standardized patient questionnaire and evaluation form. Informed Consent is obtained after a detailed discussion with the patient/family members about the project, including any potential risks of treatment.

All patient data is recorded and maintained on Standardized Case Report Forms (CRF) for subsequent data analysis and reporting. All data analysis is carried out by the (EMMES) consulting agency.

Patient exclusion criteria include:
1) Current pregnancy or lactation (baseline pregnancy test if there is any question concerning status). Also, females of child-bearing potential who are not practicing an acceptable method of contraception/abstinence, barrier method, oral contraception.
2) Age less than 18 or grater than 65.
3) MS in remission or quiescent (DSS at baseline<3.0) or extremely severe (DSS>6.5)
4) Beta interferon, glatiramer or corticosteriod therapy within 3 months prior to baseline. Immunosuppressive treatment.
5) Primary MS brain stem/visual symptoms only without spinal cord manifestations.
6) Medical conditions which may confound evaluation of BBIC treatment in MS (e.g. ALS, vasculitis, syphilis, HIV or HTLV-1 myelopathy, active thyroid disease, nutritional deficiencies, life-threatening diseases).
7) Any prior diagnosis of pancreatitis, pancreatic carcinoma, pancreatic adenoma, obstruction of pancreatic ducts, or amyloidosis.
8) Allergy, or prior adverse reaction to soybeans.
9) Patient with high levels of BBI. activity in the diet (as determined from the food frequency questionnaire, or direct measurement of BBI metabolites in blood or urine).

The BBIC used in the study contains proteins and carbohydrates, with essentially no fat. BBIC contains 100 mg/g CI activity, and 40 mg/g trypsin inhibitory activity. The CI activity in BBIC is stable over at least a 1½ year period, as is the ability of BBIC to inhibit transformation in vitro. BBIC is manufactured by Central Soya, Inc. (Ft. Wayne, Ind.) and the tablet formation prepared by Murty Pharmaceuticals, Inc. (Lexington, Ky.).

Therapy. BBIC tablets or placebo is administered orally on a daily basis, for 12 months. The BBIC of 800 CI units per day is divided into two fractions, to be taken with food two times per day in the morning and in the evening. Of the total of 20 patients in the trial, 15 receive BBIC (800 CI units/day) and 5 receive placebo in a randomized, double-blinded manner. Medications (BBIC and placebo) are dispensed by a pharmacist, who randomly assigns medication with only a coded label. Only the pharmacist knows the treatment groups to which the patients have been assigned. The pharmacist is not involved in other aspects of the trial, and will not make the code available until after all of the data from the trial have been recorded and analyzed.

Evaluation methods. Each patient is treated as an outpatient. Baseline vital signs and a physical examination are carried out before initiation of the therapeutic regimen to assess any possible contra-indications to the treatment.

| Lab safety assessments: | |
|---|---|
| a) Baseline measurements | |
| Blood Chemistries | |
| Glucose | ALT(SGPT) |
| Calcium | Total Protein |
| Urea | Albumin |
| Creatinine | Cholesterol |
| Total Bilirabin | Alkaline Phosphatase |
| AST (SGOT) | Phosphorus |
| Electrolytes | |

| Lab safety assessments: -continued | |
|---|---|
| Sodium | Potassium |
| Hematology | |
| Hemoglobin | Bands |
| Hematocrit | Lymphocytes |
| Red Blood Cells (RBC) | Monocytes |
| RBC Morphology | Eosinophils |
| White Blood Cells | Basophils |
| Neutrophils | Platelets |
| Urinalysis | |
| Protein | Glucose |
| pH | Blood |
| Serum Beta hCG, Qualitative | |

Sequential safety studies.
(1) Baseline and every 3 months—CBC, urinalysis, liver function tests, chemistry panel, sedimentation rate.
(2) Baseline and at 6 and 12 months—chest x-ray.
(3) Baseline and after one (1) year—levels of anti-mouse 1 g antibodies.
(4) Baseline and after one (1) year—serum levels and complement C4 and C3.

Clinical Assessment of MS Status.
Baseline and every 3 months:
Physical Examination-(including Vital Signs)-Medical History
Historical/Concomitant Medications
Medications
ECG
EDSS Evaluation
MSQLI
9-hole peg test
PASAT (Cognitive function test)
Timed, 25 meter ambulation test
Contrast letter acuity testing with Sloan low-contrast letter charts
Brain MRI, with gadolinium injection All adverse experiences (ADR) during the pilot study, whether or not of immediate relationship to BBIC administration, must be recorded on the Toxicities/Medical Problems of the Case Report Form.

Inflammation Studies. Evaluation of general CMI. It is generally agreed that DTH skin testing is the most cost-effective method to assess in vivo CMI (Kennedy, 1998). Extensive clinical experience indicates that 90% of healthy adults exhibit DTH reactions to one or more of a panel of 5 antigens. DTH skin testing will be conducted before treatment and at 3 month interval thereafter by practitioners who are highly experienced in the technique, with excellent interrater reliability (Kennedy et al, 1993B). Five common recall antigens are used: mumps (Connaught; 40 complement-fixing units per ml); tetanus toxoid (Wyeth; 10 Loeffler units/ml); *Candida albicans* (Greer; 500 protein nitrogen units per ml); purified protein derivative (Connaught; 5 TU), and *Trichophyton* sp. (Hollister; 1:30). In quality control studies using freshly diluted reagents, which were used well within the expiration period of the stock solutions, patterns of responses are consistent over a period of years. Repeat testing in healthy volunteers induces similar responses. A reduction of >50% in the diameter of induration at 48 hours would be evidence of significant inhibition of DTH.

To study inflammatory reactivity CRP is measured in serum samples by an inhibition enzyme-linked immunoassay (ELISA). Alpha I-antichymotrypsin (ACT) levels in serum samples are assayed using an inhibition ELISA. Purified human ACT and anti-human ACT antibodies are commercially available (Calbiochem). Normal serum ACT average about 420 mg/l. Since serum MMP-9 levels are reportedly increased shortly before MS exacerbations (Hartung et al., 2000), the effect of BBIC administration on MMP-9 levels is an important surrogate measurement of the inhibitory effect of BBIC in the enzymatic cascade. Serum MMP-9 levels will be assessed by an immunoassay, as described by Gijbels et al., 1992.

Functional determinations are measured and quantified according to the following standardizing scales to determine initial capability of the patient and to measure changes resulting from treatment.

Functional System Scale Studies (FS)

Pyramidal Functions:
0=Normal
1=Abnormal signs without disability
2=Minimal disability
3=Mild or moderate paraparesis, hemiparesis, or severe monoparesis
4=Marked paraparesis or hemiparesis, or moderate quadriparesis or monoplegia
5=Paraplegia, hemiplegia, or marked quadriparesis
6=Quadriplegia Sensory Functions:
0=Normal
1=Vibration or figure writing decrease 1 or 2 limbs
2=Mild decrease in touch or pain or position sensation and/or moderate decrease in 1 or 2 limbs; vibratory decrease alone in 3 or 4 limbs
3=Moderate decrease in touch or pain or position sensation and/or essentially lost vibration in 1 or 2 limbs; or mild decrease in touch or pain and/or moderate decrease in proprioceptive tests in 3 or 4 limbs
4=Marked decrease in touch or pain or proprioception alone or combined in 1 or 2 limbs; or moderate decrease in touch or pain and/or severe proprioceptive loss in more than 2 limbs
5=Loss of sensation in 1 or 2 limbs; or moderate decrease in touch or pain and/or loss of proprioception below the head
6=Sensation lost below the head Cerebellar Functions:
0=Normal
1=Abnormal signs without disability
2=Mild ataxia
3=Severe ataxia in all limbs
4=Unable to perform coordinated movements Bowel and Bladder Functions:
0=Normal
1=Mild urinary hesitancy, urgency, or retention
2=Moderate hesitancy, urgency, retention of bowel or bladder, or rare urinary incontinence
3=Frequent urinary incontinence
4=In need of almost constant catheterization, but with adequate bowel function
5=Loss of bladder function
6=Loss of bladder and bowel function Brain Stem Functions:
0=Normal
1=Signs only
2=Moderate nystagmus or other mild disability
3=Severe, marked extraocular weakness or moderate disability of other cranial nerves
4=Marked dysarthria or other marked disability
5=Inability to swallow or speak Mental Functions:
0=Normal
1=Mood alteration only
2=Mild decrease in mentation
3=Moderate decrease in mentation
4=Marked decrease in mentation
5=Dementia and/or chronic alertness Visual Functions:
0=Normal
1=Acuity better than 20/30 in the worse eye
2=Acuity between 20/30 and 20/59 in worse eye
3=Acuity between 20/60 and 20/99 in worse eye
4=Acuity between 10/100 and 20/200 in worse eye Grade 3 plus better eye 20/60 or less
5=Acuity 20/200 or less in worse eye or Grade 4 plus better eye 20/60 or less
6=Grade 5 plus better eye 20/60 or less Other Functions:
0=Normal
1=Any other findings (specify below)

Ambulatory determinations are measured and quantified according to the following standardizing Ambulation Index scales to determine initial capability of the patient and to measure changes resulting from treatment.

Ambulation Index
0=Asymptomatic; fully active.
1=Walks normally but reports fatigue which interferes with athletic or other demanding activities.
2=Abnormal gait or episodic imbalance; gait disorder is noticeable to family and friends. Able to walk 25 feet in 10 seconds or less.
3=Walks independently; able to walk 25 feet in 20 seconds or less.
4=Requires unilateral support (cane, single crutch) to walk; uses support more than 80% of the time. Walks 25 feet in 20 seconds or less.
5=Requires bilateral support (cane, crutches, walker) and walks 25 feet in 20 seconds or less; or, requires unilateral support but walks 25 feet in greater than 20 seconds.
6=Requires bilateral support and walks 25 feet in greater than 20 seconds. May use wheelchair on occasion.*

*The use of a wheelchair may be determined by a patient's lifestyle and motivation. It is expected that patients in grade 7 will use a wheelchair more frequently than patients in grades 5 or 6. Assignment of a grade, however, in the 5-7 range is determined by the ability of a patient to walk a given distance, and not by the extent to which a patient uses a wheelchair.

7=Walking limited to several steps with bilateral support; unable to walk 25 feet. May use wheelchair for most activities.
8=Restricted to wheelchair; able to transfer independently.
9=Restricted to wheelchair; unable to transfer independently.

To define the functional and ambulatory determinations, the Kurtzke Expanded Disability Status Scale (EDSS) in Multiple Sclerosis follows. Note: EDSS steps below 5 refer to patients who are fully ambulatory, and the precise step is defined by the Functional System (FS) score(s). EDSS steps from 5 up are defined by ability to ambulate, and usual equivalents in FS scores are provided. A mental function grade of 1 does not enter into FS score for EDSS steps. EDSS should not change by 1.0 step unless there is a change in the same direction of at least one step in at least one FS.

Kurtzke Expanded Disability Status Scale (EDSS)

0=Normal neurologic exam (all grade 0 in FS Cerebral grade I acceptable).

1.0=No disability, minimal signs in one FS 9 (i.e., grade I excluding Cerebral grade 1).

1.5=No disability, minimal signs in more than one FS (more than grade I excluding Cerebral grade 1).

2.0=Minimal disability in one FS (one FS grade 2, others 0 or 1).

2.5=Minimal disability in two FS (two FS grade 2, other 0 or 1).

3.0=Moderate disability in one FS (one FS grade 3, other 0 or 1), or mild disability in three of four Fs (three/four FS grade 2, other 0 or 1) though fully ambulatory.

3.5=Fully ambulatory but with moderate disability in one FS (one grade 30 and one or two FS grade 2; or two FS grade 3; or five FS grade 2 (others 0 or 1).

4.0=Fully ambulatory without aid, self-sufficient, up and about some 12 hours a day despite relatively severe disability consisting of one FS grade 4 (other 0 or 1), or combinations or lesser grades exceeding limits of previous steps. Able to walk without aid or rest some 500 meters.

4.5=Fully ambulatory, without aid, up and about much of the day, able to work a full day, may otherwise have some limitation of full activity or require minimal assistance; characterized by relatively severe disability, usually consisting of one FS grade 4 (others 0 or 1), or combinations or lesser grades exceeding limits of previous steps. Able to walk without aid or rest for some 300 meters.

5.0=Ambulatory without aid or rest for about 200 meters; disability severe enough to impair full daily activities (e.g., to work a full day without special provisions). Usual FS equivalents are one grade 5 alone, other 0 or 1; or combinations of lesser grades usually exceeding specifications for step 4.0.

5.5=Ambulatory without aid or rest for about 100 meters; disability severe enough to preclude full daily activities. Usual FS equivalents are one grade 5 alone, others 0 or 1; or combinations of lesser grades usually exceeding those for step 4.0.

6.0=Intermittent or unilateral constant assistance (cane, crutch, etc.) required to walk about 100 meters, with or without rest. Usual FS equivalents are combinations with more than two FS grade 3+.

6.5=Constant bilateral assistance required to walk about 20 meters without resting. Usual FS equivalents are combinations with more than two FS grade 3+.

7.0=Unable to walk beyond about 5 meters even with aid, essentially restricted to wheelchair; wheels self in standard wheelchair and transfers alone; up and about in w/c some 12 hours a day. Usual FS equivalents are combinations with more than one FS grade 4; very rarely pyramidal grade 5 alone.

7.5=Unable to take more than a few steps; restricted to wheelchair, may need aid in transfer; wheels self but cannot carry on in standard wheelchair a fall day; may require motorized wheelchair. Usual FS equivalents are combinations with more than one FS grade 4+.

8.0=Essentially restricted to bed or chair or perambulated in wheelchair; may be out of bed itself much of the day; retains many self-care functions; generally has effective use of arms. Usual FS equivalents are combinations, generally grade 4+in several systems.

8.5=Essentially restricted to bed or chair or perambulated in wheelchair; may be out of bed much of the day; retains many self-care functions; generally has effective use of arms. Usual FS equivalents are combinations, generally grade 4+in several systems.

8.5=Essentially restricted to bed much of the day; has some effective use of arms; retains some self-care functions. Usual FS equivalents are combinations, generally 4+in several systems.

9.0=Helpless bed patient; can communicate and eat. Usual FS equivalents are combinations, mostly grade 4+.

9.5=Totally helpless bed patient; unable to communicate effectively or eat/swallow. Usual FS equivalents are combinations, almost all grade 4+.

10.0=Death due to MS.

Cognitive Function is measured and standardized initially and throughout treatment by the Paced Auditory Serial Addition Test (PASAT), which provides a measure of sustained attention and information processing speed. It was originally devised by Gronwall and colleagues (Gronwall, 1977; Gronwall & Wrightson, 1974, herein incorporated by reference) to measure the acute effects of minor head injury. The test requires the use of a cassette tape recorder and a prerecorded tape, which may be purchased with the Brief, Repeatable Battery. Two alternate forms of this test have been developed, although practice effects should not be a problem with this test.

Manual dexterity is measured and quantified according to the following standardized 9-Hole Peg Test to determine initial capability of the patient and to measure changes resulting from treatment.

9-Hole Peg Test

Pegboard is centered in front of subject with pegs placed in the container next to the board on the same side as the hand being tested. The dominant hand is tested first. While the examiner briefly demonstrates the test, the patient is instructed to pick up the pegs one at a time, using the dominant hand only, and to put the pegs into the holes in any order until all of the holes are filled. Then the patient is to remove pegs one at a time, and return them to the container. The goal is to move as quickly as possible through the test. A practice test is given first, followed by the actual test, during which the patient is told to go faster.

The stopwatch is started by the examiner as soon as the subject touches the first peg, and is stoped when the last peg hits the container, and the time is recorded in seconds. Then the container is placed on the opposite side of the pegboard and the patient's other hand is tested. There are two trials per hand. Maximum time to complete one trial is 5 minutes (300 seconds). For patients with upper extremity tremors or truncal ataxias, stabilization of elbows on the table surface may be used.

Following completion of the clinical trial, the method of using BBI/BBIC defined herein, is applied to treat patients with chronic inflammatory autoimmune diseases, such as rheumatoid arthritis, particularly those patients with chronic neuroinflammatory autoimmune diseases, such as MS or GBS. The tests and standards provided herein provide measures for determining levels of improvement in the patient as the inflammation is reduced, suppressed, alleviated or eliminated as a result of the BBI/BBIC treatment.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the spirit and scope of the invention. Such modifications, equivalent variations and additional embodiments are also intended to fall within the scope of the appended claims.

What is claimed is:

1. A method for treating inflammation in an animal model of an induced inflammatory disease comprising administering to the animal model an amount of Bowman Birk Inhibitor effective to reduce, inhibit, suppress or prevent a chronic inflammation.

2. The method of claim 1, wherein the inflammation is chronic inflammation of neural tissue.

3. The method of claim 1, wherein the inflammation affects the central nervous system or peripheral nervous system of the animal model.

4. The method of claim 3, wherein demyelination of nerve tissue of the animal model is reduced, inhibited, suppressed or prevented.

5. The method of claim 1, wherein the disease is Experimental Autoimmune Encephalomyelitis or Experimental Autoimmune Neuritis.

6. The method of claim 5, wherein the Bowman Birk Inhibitor is administered orally as Bowman Birk Inhibitor Concentrate.

* * * * *